(12) United States Patent
Lanos et al.

(10) Patent No.: US 10,612,016 B2
(45) Date of Patent: *Apr. 7, 2020

(54) VARIANT OF D-PSICOSE 3-EPIMERASE AND USES THEREOF

(71) Applicant: Roquette Freres, Lestrem (FR)

(72) Inventors: Pierre Lanos, La Bassee (FR); Liuming Zhou, Geneva, IL (US); Min Jia, Dezhou (CN); Wenli Zhang, Tengzhou (CN); Bo Jiang, Zhenjiang Province (CN); Wanmeng Mu, Wuxi (CN); Tao Zhang, Wuxi (CN)

(73) Assignee: ROQUETTE FRERES, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,418

(22) Filed: Oct. 13, 2017

(65) Prior Publication Data

US 2018/0179510 A1 Jun. 28, 2018

Related U.S. Application Data

(62) Division of application No. 14/914,264, filed as application No. PCT/EP2014/068628 on Sep. 2, 2014, now Pat. No. 9,790,481.

(30) Foreign Application Priority Data

Sep. 3, 2013 (EP) ..................................... 13306195
Feb. 14, 2014 (EP) ..................................... 14305199

(51) Int. Cl.
| | |
|---|---|
| *C12N 1/21* | (2006.01) |
| *C12N 9/90* | (2006.01) |
| *C12P 19/24* | (2006.01) |
| *C12P 19/02* | (2006.01) |
| *A23L 33/135* | (2016.01) |
| *A23L 5/00* | (2016.01) |
| *A23L 29/30* | (2016.01) |
| *A23L 33/13* | (2016.01) |

(52) U.S. Cl.
CPC .................. *C12N 9/90* (2013.01); *A23L 5/00* (2016.08); *A23L 29/30* (2016.08); *A23L 33/13* (2016.08); *C12P 19/02* (2013.01); *C12P 19/24* (2013.01); *C12Y 501/03* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2009/0081726 A1† | 3/2009 | Kodama | |
| 2010/0129865 A1 | 5/2010 | Maruta et al. | |
| 2012/0244580 A1† | 9/2012 | Hung | |
| 2014/0199732 A1 | 7/2014 | Kim et al. | |

FOREIGN PATENT DOCUMENTS

| | | |
|---|---|---|
| CN | 102 373 230 | 3/2012 |
| EP | 1 956 088 | 8/2008 |
| WO | WO-2006/129954 | 12/2006 |
| WO | WO-2011/040708 | 4/2011 |
| WO | WO-2013/027999 | 2/2013 |

OTHER PUBLICATIONS

Guo et al., Protein tolerance to random amino acid change, Proc. Natl. Acad. Sci. USA, 2004, 101, 9205-10.*
Chan, H.-C., et al., "Crystal structures of o-psicose 3-epimerase from *Clostridium cellulolyticum* H10 and its complex with ketohexose sugars," *Protein & Cell*, Feb. 2012, vol. 3, No. 2. pp. 123-131.
Choi, J.-G., et al., "Improvement in the Thermostability of o-Psicose 3-Epimerase from *Agrobacterium tumefaciens* by Random and Site-Directed Mutagenesis," *Applied and Environmental Microbiology*, Oct. 15, 2011, vol. 77, No. 20, pp. 7316-7320.
Database UniProt, XP-002716904, "SubName: Full=AP endonuclease, family 2;", Database Accession No. D3AJP4, Mar. 23, 2010, p. 1.
Izumori, K., et al., "A New Enzyme, o-Ketohexose 3-Epimerase, from Pseudomonas sp. ST-24," Bioscience, Biotechnology, and Biochemistry, 1993, vol. 57, No. 6, pp. 1037-1039.
Jia, M., et al., "A D-psicose 3-epimerase with neutral pH optimum from *Clostridium bolteae* for o-psicose production: cloning, expression, purification, and characterization," *Applied Microbioloav and Biotechnoloav*, May 4, 2013, pp. 1-9.
Kim, H.-J., et al., "Characterization of an *Agrobacterium tumefaciens* o-Psicose 3-Epimerase That Converts o-Fructose to o-Psicose," *Applied and Environmental Microbiology*, Feb. 2006, vol. 72, No. 2, pp. 981-985.
Kim, H.-J., et al., "Mutational analysis of the active site residues of a o-psicose 3-epimerase from *Agrobacterium tumefaciens*," *Biotechnology Letters*, 2010, vol. 32, No. 2, pp. 261-268.
Kim, H.J. et al. "Roles of Ile66 and Ala107 of 0-psicose 3-epimerase from Agrobacterium tumefaciens in binding 06 of its substrate, 0-fructose" Biotechnol Lett, 2010, pp. 113-118, vol. 32.
Kim, K. et al. "Crystal Structure of D-Psicose 3-epimerase from Agrobacterium tumefaciens and its Complex with True Substrate 0-Fructose: A Pivotal Role of Metal in Catalysis, an Active Site for the Non-phosphorylated Substrate, and its Conformational Changes" *J. Mol. Biol.*, 2006, pp. 920-931, vol. 361.
Lim, B.-C., et al., "A stable immobilized o-psicose 3-epimerase for the production of o-psicose in the presence of borate," Process Biochemistry, 2009, vol. 44, pp. 822-828.
Mu, W., et al., "Characterization of a o-psicose-producing enzyme, o-psicose 3-epimerase, from *Clostridium* sp.," *Biotechnology Letters*, 2013, vol. 35, No. 2, pp. 1481-1486.

(Continued)

Primary Examiner — Robert B Mondesi
Assistant Examiner — Todd M Epstein
(74) *Attorney, Agent, or Firm* — Oliff PLC

(57) ABSTRACT

The present invention relates to an improved variant of a D-psicose 3-epimerase and its uses.

25 Claims, 6 Drawing Sheets

Specification includes a Sequence Listing.

(56) References Cited

OTHER PUBLICATIONS

Mu, W., et al., "Cloning, Expression, and Characterization of a D-Psicose 3-Epimerase from *Clostridium cellulolyticum* 10," *Journal of Agricultural and Food Chemistry*, 2011, vol. 59, pp. 7785-7792.

Oshima, H., et al., "Psicose Contents in Various Food Products and its Origin," *Food Science and Technology Research*, 2006, vol. 12, No. 2, pp. 137-143.

Smith, J.A., "Immunology," *Current Protocols in Molecular Biology*, Chapter 11, Supplement 72, pp. 11.0.1-11.18.9, 2005.

Uniprot, Accession No. U4R1A7, 2013, www.uniprot.org. <http://www.uniprot.org/>.

Written Opinion in International Application No. PCT/EP2014/068628, dated Dec. 1, 2014, pp. 1-7.

Zhang et al., "Substrate-binding site of D-psicose 3-epimerase from *Ruminococcus* sp.," *Microbiol. China*, 2014, 41, pp. 811-817.

Zhang, L., et al., "Characterization of D-tagatose-3-epimerase from *Rhodobacter sphaeroides* that converts D-fructose into D-psicose," *Biotechnology Letters*, 2009, vol. 31, pp. 857-862.

Zhang, W., et al., "Characterization of a Novel Metal-Dependent D-Psicose 3-Epimerase from Clostridium scindens 35704," *PLOS ONE*, Apr. 30, 2013, vol. 8, No. 4, p. e62987, pp. 1-9.

Zhu, Y., et al., "Overexpression of D-psicose 3-epimerase from *Ruminococcus* sp. in *Escherichia coli* and its potential application in D-psicose production," *Biotechnology Letters*, 2012, vol. 34, pp. 1901-1906.

UniProtKB/Swiss-Prot Accession No. O50580.1, D-tagatose 3-epimerase, Aug. 10, 2000.†

GenBank Accession No. EDP19602.1, hypothetical protein CLOBOL [[Clostridium] bolteae ATCC BAA-613], Oct. 18, 2007.†

GenBank Accession No. EES75522.1, hypothetical protein RSAG_03412 [*Ruminococcus* sp. 5_1_39BFAA], Jul. 8, 2009.†

GenPept Accession No. 3VNI_A, Chain A, Xylose Isomerase Domain Protein Tim Barrel, Aug. 1, 2012.†

NCBI Reference Sequence: NP_355915.1, D-psicose 3-epimerase [Agrobacterium fabrum str. C58], Oct. 3, 2001.†

GenBank Accession No. EDS06411.1, AP endonuclease, family 2 [[Clostridium] scindens ATCC 35704], Feb. 12, 2008.†

Choi et al. "Improvement in the Thermostability of D-Psciose 3-Epimerase from Agrobacterium Tumiefaciens by Random and Site-Directed Mutagenesis." Applied and Environmental Microbiology, 77(20): 7316-20 (2011), Oct. 2011.†

Chan et al. "Crystal structures of D-psicose 3-epimerase from Clostridium cellulolyticum H10 and its complex with ketohexose sugars." Protein Cell, 3(2): 123-31 (2012), Feb. 2012.†

Zhang et al. "Characterization of a Novel Metal-Dependent D-Psicose 3-Epimerase from Clostridium scindens 35704." PLOS ONE, 8(4): e62987 (2013) Apr. 2013.†

\* cited by examiner
† cited by third party

```
Clce-DPEase    ----------MKHGIYYAYWEQEWEADYKYYIEKVAKLGFDILEIAASPLPFYS--DIQI  48
Clsp-DPEase    ----------MKHGIYYAYWEQEWEADYKYYIEKVAKLGFDILEIAASPLPFYS--DNQI  48
Clsc-DPEase    ----------MKHGIYYAYWEQEWAADYKRYVEKAAKLGFDILEVGAAPLPDYS--AQEV  48
Agtu-DPEase    ----------MKHGIYYSYWEHEWSAKFGPYIEKVAKLGFDIIEVAAHHINEYS--DAEL  48
Rusp-DPEase    ----------MKYGIYYAYWEKEWNGDYKYYIDKISKLGFDILEISCGAFSDYYTKDQEL  50
Clbo-DPEase    MRYFKEEVAGMKYGIYFAYWTKEWFADYKKYMDKVSALGFDVLEISCAALRDVYTTKEQL  60
Psci-DTEase    ---------MNKVGMFYTYWSTEWMVDFPATAKRIAGLGFDLMEISLGEFHNLS--DAKK  49
Rhsp-DTEase    --------MKNPVGIISMQFIRPFTSESLHFLKKSRALGFDFIELLVPEPEDGL----DA  48
                         *:     :    :     .:    ****.:*:              .

Clce-DPEase    NELKACAHGNGITLTVGHGPSAEQNLSSPDPDIRKNAKAFYTDLLKRLYKLDVHLIGGAL 108
Clsp-DPEase    NELKACARGNGITLTVGHGPSAEQNLSSPDPYIRKNAKAFYTDLLKRLYKLDVHLIGGAI 108
Clsc-DPEase    KELKKCADDNGIQLTAGYGPAFNHNMGSSDPKIREEALQWYKRLFEVMAGLDIHLIGGAL 108
Agtu-DPEase    ATIRKSAKDNGIILTAGIGPSKTKNLSSEDAAVRAAGKAFFERTLSNVAKLDIHTIGGAL 108
Rusp-DPEase    IDIGKYAKEKGVTLTAGYGPHFNESLSSSEPNTQKQAISFWKETLRKLKLMDIHIVGGAL 110
Clbo-DPEase    IELREYAKEKGLVLTAGYGPTKAENLCSEDPEAVRRAMTFFKDLLPKLQLMDIHILGGGL 120
Psci-DTEase    RELKAVADDLGLTVMCCIGLKSEYDFASPDKSVRDAGTEYVKRLLDDCHLLGAPVFAGLT 109
Rhsp-DTEase    AEVRRICEGEGLGLVLAARVNLQRSIASEEAAARAGGRDYLKYCIEAAEALGATIVGGPL 108
                   .   *:  :         .: *  :        :       : :     ..*

Clce-DPEase    YSY-----WPIDYTKTIDKKGDW-ERSVESVREVAKVAEACGVDFCLEVLNRFENYLINT 162
Clsp-DPEase    YSY-----WPVDYTKTIDKKGDW-ERSVESVREVAQVAEACGVDFCLEVLNRFENYLINT 162
Clsc-DPEase    YSY-----WPVDFA-TANKEEDW-KHSVEGMQILAPIASQYGINLGMEVLNRFESHILNT 161
Agtu-DPEase    HSY-----WPIDYSQPVDKAGDY-ARGVEGINGIADFANDLGINLCIEVLNRFENHVLNT 162
Rusp-DPEase    YGY-----WPVDYSKPFDKKRDL-ENSIKNMKIISQYAEEYDIMMGMEVLNRFEGYMLNT 164
Clbo-DPEase    YSY-----WPVDFTINNDKQGDR-ARAVRNLRELSKTAEECDVVLGMEVLNRYEGYILNT 174
Psci-DTEase    FCA-----WPQSPPLDMKDKRPYVDRAIESVRRVIKVAEDYGIIYALEVVNRFEQWLCND 164
Rhsp-DTEase    YGEPLVFAGRPPFPWTAEQIATRAARTVEGLAEVAPLAASAGKVFGLEPLNRFETDIVNT 168
                .       .    .  ..   :::   :       .   :*   :* :**:*   : *

Clce-DPEase    AQEGVDFVKQVDHNNVKVMLDTFHMNIEEDSIGGAIRTAGSYLGHLHTGECNRKVPGRGR 222
Clsp-DPEase    AQEGVDFVKQVGHDNVKVMLDTFHMNIEEDSIGGAIRTAGSYLGHLHTGECNRKVPGKGR 222
Clsc-DPEase    SEEGVKFVTEVGMDNVKVMLDTFHMNIEESSIGDAIRHAGKLLGHFHTGECNRMVPGKGR 221
Agtu-DPEase    AAEGVAFVKDVGKNNVKVMLDTFHMNIEEDSFGDAIRTAGPLLGHFHTGESNRRVPGKGR 222
Rusp-DPEase    CDEALAYVEEVGSSNVGVMLDTFHMNIEEDNIAAAIRKAGDRLYHFHIGEGNRKVPGKGM 224
Clbo-DPEase    CEEAIDFVDEIGSSHVKIMLDTFHMNIEETNMADAIRKAGDRLGHLHLGEQNRLVPGKGS 234
Psci-DTEase    AKEAIAFADAVDSPACKVQLDTFHMNIEETSFRDAILACKGKMGHFHLGEANRLPPGEGR 224
Rhsp-DTEase    TAQAIEVVDAVGSPGLGVMLDTFHMNMEERSIPDAIRATGARLVHFQANENHRGFPGTGT 228
                ::  .   .  :      :*******:**  .:  **      : *:: .* :* ** *

Clce-DPEase    IPWVEIGEALADIGYNGSVVMEPFVRMGGTVGSNIKVWRDISNGADEKMLDREAQAALDF 282
Clsp-DPEase    IPWIEIGEALADIGYNGSVVMEPFVRMGGTVGSNIKVWRDISNGADEEKLDREAQAALNF 282
Clsc-DPEase    TPWREIGDALREIEYDGTVVMEPFVRMGGQVGSDIKVWRDISKGAGEDRLDEDARRAVEF 281
Agtu-DPEase    MPWHEIGLALRDINYTGAVIMEPFVKTGGTIGSDIKVWRDLSGGADIAKMDEDARNALAF 282
Rusp-DPEase    LPWNEIGQALRDINYQHAAVMEPFVMQGGTVGHDIKIWRDIIGNCSEVTLDMDAQSALHF 284
Clbo-DPEase    LPWAEIGQALRDINYQGAAVMEPFVMQGGTIGSEIKVWRDMVPDLSEEALDRDAKGALEF 294
Psci-DTEase    LPWDEIFGALKEIGYDGTIVMEPFMRKGGSVSRAVGVWRDMSNGATDEEMDERARRSLQF 284
Rhsp-DTEase    MDWTAIARALGQAGYAGPVSLEPFRRDDERVALPIAHWR-----APHEDEDEKLRAGLGL 283
                 * * **:    *  .  :***   .::  :  :  **         *  :.: :

Clce-DPEase    SRYVLECHKHS-  293
Clsp-DPEase    SRYVLGNRKL--  292
Clsc-DPEase    QRYMLEWK----  289
Agtu-DPEase    SRFVLGG-----  289
Rusp-DPEase    VKHVFEV-----  291
Clbo-DPEase    CRHVFGI-----  301
Psci-DTEase    VRDKLA------  290
Rhsp-DTEase    IRSAITLAEVTH  295
                :  :
```

FIGURE 1

SEQUENCE LISTING

```
<160> NUMBER OF SEQ ID NOS: 20

<210> SEQ ID NO 1
<211> LENGTH: 879
<212> TYPE: DNA
<213> ORGANISM: Clostridium cellulolyticum
<220> FEATURE:
<221> NAME/KEY: CDS
<222> LOCATION: (1)..(879)

<400> SEQUENCE: 1 atg aaa cat ggt ata tac tac gca tat tgg gaa caa gaa tgg gaa gct        48
Met Lys His Gly Ile Tyr Tyr Ala Tyr Trp Glu Gln Glu Trp Glu Ala
1               5                   10                  15 gat tac aaa tac tat att gag aag gtt gca aag ctt ggt ttt gat att        96
Asp Tyr Lys Tyr Tyr Ile Glu Lys Val Ala Lys Leu Gly Phe Asp Ile
                20                  25                  30 cta gag att gca gct tca ccg cta cct ttt tac agt gac att cag att       144
Leu Glu Ile Ala Ala Ser Pro Leu Pro Phe Tyr Ser Asp Ile Gln Ile
            35                  40                  45 aat gag ctc aag gca tgt gcc cat ggc aat gga att aca ctt acg gta       192
Asn Glu Leu Lys Ala Cys Ala His Gly Asn Gly Ile Thr Leu Thr Val
        50                  55                  60 ggc cat ggg cct agt gca gaa caa aac ctg tct tct ccc gac ccc gat       240
Gly His Gly Pro Ser Ala Glu Gln Asn Leu Ser Ser Pro Asp Pro Asp
65                  70                  75                  80 att cgc aaa aat gct aaa gct ttt tat acc gat tta ctc aaa cga ctt       288
Ile Arg Lys Asn Ala Lys Ala Phe Tyr Thr Asp Leu Leu Lys Arg Leu
                85                  90                  95 tac aag ctg gat gta cat ttg ata ggt ggg gct tta tat tct tat tgg       336
Tyr Lys Leu Asp Val His Leu Ile Gly Gly Ala Leu Tyr Ser Tyr Trp
                100                 105                 110
```

```
ccg ata gat tac aca aag aca att gat aaa aaa ggc gat tgg gaa cgc      384
Pro Ile Asp Tyr Thr Lys Thr Ile Asp Lys Lys Gly Asp Trp Glu Arg
    115                 120                 125 agc gtt gaa agt gtt cga gaa gtt gct aag gtg gcc gaa gcc tgt gga      432
Ser Val Glu Ser Val Arg Glu Val Ala Lys Val Ala Glu Ala Cys Gly
130                 135                 140 gtg gat ttc tgc cta gag gtt ctt aat aga ttt gag aat tat tta att      480
Val Asp Phe Cys Leu Glu Val Leu Asn Arg Phe Glu Asn Tyr Leu Ile
145                 150                 155                 160 aac aca gca caa gag ggt gta gat ttt gta aaa cag gtt gac cat aac      528
Asn Thr Ala Gln Glu Gly Val Asp Phe Val Lys Gln Val Asp His Asn
                165                 170                 175 aat gta aag gta atg ctt gat acc ttc cac atg aat att gag gaa gat      576
Asn Val Lys Val Met Leu Asp Thr Phe His Met Asn Ile Glu Glu Asp
        180                 185                 190 agt atc gga ggt gca atc agg act gcg ggc tct tac ttg gga cat tta      624
Ser Ile Gly Gly Ala Ile Arg Thr Ala Gly Ser Tyr Leu Gly His Leu
            195                 200                 205 cac act ggc gaa tgt aat cgt aaa gtt ccc ggc aga gga aga att cca      672
His Thr Gly Glu Cys Asn Arg Lys Val Pro Gly Arg Gly Arg Ile Pro
    210                 215                 220 tgg gta gaa att ggt gag gct ctt gct gac ata ggt tat aac ggt agt      720
Trp Val Glu Ile Gly Glu Ala Leu Ala Asp Ile Gly Tyr Asn Gly Ser
225                 230                 235                 240 gtt gtt atg gaa cct ttt gtt aga atg ggc gga act gtc gga tct aat      768
Val Val Met Glu Pro Phe Val Arg Met Gly Gly Thr Val Gly Ser Asn
                245                 250                 255 att aag gtt tgg cgt gac att agt aac ggt gca gat gag aaa atg ctg      816
Ile Lys Val Trp Arg Asp Ile Ser Asn Gly Ala Asp Glu Lys Met Leu
        260                 265                 270 gat aga gaa gca cag gcc gca ctt gat ttc tcc aga tat gta tta gaa      864
Asp Arg Glu Ala Gln Ala Ala Leu Asp Phe Ser Arg Tyr Val Leu Glu
            275                 280                 285 tgt cat aaa cac tcc                                                  879
Cys His Lys His Ser
        290

<210> SEQ ID NO 2
<211> LENGTH: 293
<212> TYPE: PRT
<213> ORGANISM: Clostridium cellulolyticum

<400> SEQUENCE: 2

Met Lys His Gly Ile Tyr Tyr Ala Tyr Trp Glu Gln Glu Trp Glu Ala
1               5                   10                  15

Asp Tyr Lys Tyr Tyr Ile Glu Lys Val Ala Lys Leu Gly Phe Asp Ile
            20                  25                  30

Leu Glu Ile Ala Ala Ser Pro Leu Pro Phe Tyr Ser Asp Ile Gln Ile
        35                  40                  45

Asn Glu Leu Lys Ala Cys Ala His Gly Asn Gly Ile Thr Leu Thr Val
    50                  55                  60

Gly His Gly Pro Ser Ala Glu Gln Asn Leu Ser Ser Pro Asp Pro Asp
65                  70                  75                  80

Ile Arg Lys Asn Ala Lys Ala Phe Tyr Thr Asp Leu Leu Lys Arg Leu
                85                  90                  95

Tyr Lys Leu Asp Val His Leu Ile Gly Gly Ala Leu Tyr Ser Tyr Trp
            100                 105                 110

Pro Ile Asp Tyr Thr Lys Thr Ile Asp Lys Lys Gly Asp Trp Glu Arg
        115                 120                 125
```

```
Ser Val Glu Ser Val Arg Glu Val Ala Lys Val Ala Glu Ala Cys Gly
    130                 135                 140
Val Asp Phe Cys Leu Glu Val Leu Asn Arg Phe Glu Asn Tyr Leu Ile
145                 150                 155                 160
Asn Thr Ala Gln Glu Gly Val Asp Phe Val Lys Gln Val Asp His Asn
                165                 170                 175
Asn Val Lys Val Met Leu Asp Thr Phe His Met Asn Ile Glu Glu Asp
                180                 185                 190
Ser Ile Gly Gly Ala Ile Arg Thr Ala Gly Ser Tyr Leu Gly His Leu
            195                 200                 205
His Thr Gly Glu Cys Asn Arg Lys Val Pro Gly Arg Gly Arg Ile Pro
    210                 215                 220
Trp Val Glu Ile Gly Glu Ala Leu Ala Asp Ile Gly Tyr Asn Gly Ser
225                 230                 235                 240
Val Val Met Glu Pro Phe Val Arg Met Gly Gly Thr Val Gly Ser Asn
                245                 250                 255
Ile Lys Val Trp Arg Asp Ile Ser Asn Gly Ala Asp Glu Lys Met Leu
                260                 265                 270
Asp Arg Glu Ala Gln Ala Ala Leu Asp Phe Ser Arg Tyr Val Leu Glu
            275                 280                 285
Cys His Lys His Ser
        290

<210> SEQ ID NO 3
<211> LENGTH: 879
<212> TYPE: DNA
<213> ORGANISM: artificial sequence
<220> FEATURE:
<223> OTHER INFORMATION: CC-DPEase variant
<220> FEATURE:
<221> NAME/KEY: CDS
<222> LOCATION: (1)..(879)

<400> SEQUENCE: 3 atg aaa cat ggt ata tac tac gca tat tgg gaa caa gaa tgg gaa gct      48
Met Lys His Gly Ile Tyr Tyr Ala Tyr Trp Glu Gln Glu Trp Glu Ala
1               5                   10                  15 gat tac aaa tac tat att gag aag gtt gca aag ctt ggt ttt gat att      96
Asp Tyr Lys Tyr Tyr Ile Glu Lys Val Ala Lys Leu Gly Phe Asp Ile
                20                  25                  30 cta gag att gca gct tca ccg cta cct ttt tac agt gac att cag att     144
Leu Glu Ile Ala Ala Ser Pro Leu Pro Phe Tyr Ser Asp Ile Gln Ile
            35                  40                  45 aat gag ctc aag gca tgt gcc cat ggc aat gga att aca ctt acg gta     192
Asn Glu Leu Lys Ala Cys Ala His Gly Asn Gly Ile Thr Leu Thr Val
50                  55                  60 ggc cat ggg cct agt gca gaa caa aac ctg tct tct ccc gac ccc gat     240
Gly His Gly Pro Ser Ala Glu Gln Asn Leu Ser Ser Pro Asp Pro Asp
65                  70                  75                  80 att cgc aaa aat gct aaa gct ttt tat acc gat tta ctc aaa cga ctt     288
Ile Arg Lys Asn Ala Lys Ala Phe Tyr Thr Asp Leu Leu Lys Arg Leu
                85                  90                  95 tac aag ctg gat gta cat ttg ata ggt ggg gct tta tat tct tat tgg     336
Tyr Lys Leu Asp Val His Leu Ile Gly Gly Ala Leu Tyr Ser Tyr Trp
                100                 105                 110 ccg ata gat tac aca aag aca att gat aaa aaa ggc gat tgg gaa cgc     384
Pro Ile Asp Tyr Thr Lys Thr Ile Asp Lys Lys Gly Asp Trp Glu Arg
            115                 120                 125
```

```
agc gtt gaa agt gtt cga gaa gtt gct aag gtg gcc gaa gcc tgt gga    432
Ser Val Glu Ser Val Arg Glu Val Ala Lys Val Ala Glu Ala Cys Gly
130                 135                 140 gtg gat ttc tgc cta gag gtt ctt aat aga ttt gag aat tat tta att    480
Val Asp Phe Cys Leu Glu Val Leu Asn Arg Phe Glu Asn Tyr Leu Ile
145                 150                 155                 160 aac aca gca caa gag ggt gta gat ttt gta aaa cag gtt gac cat aac    528
Asn Thr Ala Gln Glu Gly Val Asp Phe Val Lys Gln Val Asp His Asn
                165                 170                 175 aat gta aag gta atg ctt gat acc ttc cac atg aat att gag gaa gat    576
Asn Val Lys Val Met Leu Asp Thr Phe His Met Asn Ile Glu Glu Asp
            180                 185                 190 agt atc gga ggt gca atc agg act gcg ggc tct tac ttg gga cat tta    624
Ser Ile Gly Gly Ala Ile Arg Thr Ala Gly Ser Tyr Leu Gly His Leu
        195                 200                 205 cac act agc gaa tgt aat cgt aaa gtt ccc ggc aga gga aga att cca    672
His Thr Ser Glu Cys Asn Arg Lys Val Pro Gly Arg Gly Arg Ile Pro
    210                 215                 220 tgg gta gaa att ggt gag gct ctt gct gac ata ggt tat aac ggt agt    720
Trp Val Glu Ile Gly Glu Ala Leu Ala Asp Ile Gly Tyr Asn Gly Ser
225                 230                 235                 240 gtt gtt atg gaa cct ttt gtt aga atg ggc gga act gtc gga tct aat    768
Val Val Met Glu Pro Phe Val Arg Met Gly Gly Thr Val Gly Ser Asn
                245                 250                 255 att aag gtt tgg cgt gac att agt aac ggt gca gat gag aaa atg ctg    816
Ile Lys Val Trp Arg Asp Ile Ser Asn Gly Ala Asp Glu Lys Met Leu
            260                 265                 270 gat aga gaa gca cag gcc gca ctt gat ttc tcc aga tat gta tta gaa    864
Asp Arg Glu Ala Gln Ala Ala Leu Asp Phe Ser Arg Tyr Val Leu Glu
        275                 280                 285 tgt cat aaa cac tcc                                                879
Cys His Lys His Ser
    290

<210> SEQ ID NO 4
<211> LENGTH: 293
<212> TYPE: PRT
<213> ORGANISM: artificial sequence
<220> FEATURE:
<223> OTHER INFORMATION: Synthetic Construct

<400> SEQUENCE: 4

Met Lys His Gly Ile Tyr Tyr Ala Tyr Trp Glu Gln Glu Trp Glu Ala
1               5                   10                  15

Asp Tyr Lys Tyr Tyr Ile Glu Lys Val Ala Lys Leu Gly Phe Asp Ile
            20                  25                  30

Leu Glu Ile Ala Ala Ser Pro Leu Pro Phe Tyr Ser Asp Ile Gln Ile
        35                  40                  45

Asn Glu Leu Lys Ala Cys Ala His Gly Asn Gly Ile Thr Leu Thr Val
    50                  55                  60

Gly His Gly Pro Ser Ala Glu Gln Asn Leu Ser Ser Pro Asp Pro Asp
65                  70                  75                  80

Ile Arg Lys Asn Ala Lys Ala Phe Tyr Thr Asp Leu Leu Lys Arg Leu
                85                  90                  95

Tyr Lys Leu Asp Val His Leu Ile Gly Gly Ala Leu Tyr Ser Tyr Trp
            100                 105                 110

Pro Ile Asp Tyr Thr Lys Thr Ile Asp Lys Lys Gly Asp Trp Glu Arg
        115                 120                 125

Ser Val Glu Ser Val Arg Glu Val Ala Lys Val Ala Glu Ala Cys Gly
```

```
            130                 135                 140
Val Asp Phe Cys Leu Glu Val Leu Asn Arg Phe Glu Asn Tyr Leu Ile
145                 150                 155                 160

Asn Thr Ala Gln Glu Gly Val Asp Phe Val Lys Gln Val Asp His Asn
                165                 170                 175

Asn Val Lys Val Met Leu Asp Thr Phe His Met Asn Ile Glu Glu Asp
                180                 185                 190

Ser Ile Gly Gly Ala Ile Arg Thr Ala Gly Ser Tyr Leu Gly His Leu
                195                 200                 205

His Thr Ser Glu Cys Asn Arg Lys Val Pro Gly Arg Gly Arg Ile Pro
    210                 215                 220

Trp Val Glu Ile Gly Glu Ala Leu Ala Asp Ile Gly Tyr Asn Gly Ser
225                 230                 235                 240

Val Val Met Glu Pro Phe Val Arg Met Gly Thr Val Gly Ser Asn
                245                 250                 255

Ile Lys Val Trp Arg Asp Ile Ser Asn Gly Ala Asp Glu Lys Met Leu
                260                 265                 270

Asp Arg Glu Ala Gln Ala Ala Leu Asp Phe Ser Arg Tyr Val Leu Glu
    275                 280                 285

Cys His Lys His Ser
    290

<210> SEQ ID NO 5
<211> LENGTH: 292
<212> TYPE: PRT
<213> ORGANISM: Clostridium sp.

<400> SEQUENCE: 5

Met Lys His Gly Ile Tyr Tyr Ala Tyr Trp Glu Gln Glu Trp Glu Ala
1               5                   10                  15

Asp Tyr Lys Tyr Tyr Ile Glu Lys Val Ala Lys Leu Gly Phe Asp Ile
                20                  25                  30

Leu Glu Ile Ala Ala Ser Pro Leu Pro Phe Tyr Ser Asp Asn Gln Ile
            35                  40                  45

Asn Glu Leu Lys Ala Cys Ala Arg Gly Asn Gly Ile Thr Leu Thr Val
        50                  55                  60

Gly His Gly Pro Ser Ala Glu Gln Asn Leu Ser Ser Pro Asp Pro Tyr
65                  70                  75                  80

Ile Arg Lys Asn Ala Lys Ala Phe Tyr Thr Asp Leu Leu Lys Arg Leu
                85                  90                  95

Tyr Lys Leu Asp Val His Leu Ile Gly Gly Ala Ile Tyr Ser Tyr Trp
                100                 105                 110

Pro Val Asp Tyr Thr Lys Thr Ile Asp Lys Lys Gly Asp Trp Glu Arg
            115                 120                 125

Ser Val Glu Ser Val Arg Glu Val Ala Gln Val Ala Glu Ala Cys Gly
    130                 135                 140

Val Asp Phe Cys Leu Glu Val Leu Asn Arg Phe Glu Asn Tyr Leu Ile
145                 150                 155                 160

Asn Thr Ala Gln Glu Gly Val Asp Phe Val Lys Gln Val Gly His Asp
                165                 170                 175

Asn Val Lys Val Met Leu Asp Thr Phe His Met Asn Ile Glu Glu Asp
                180                 185                 190

Ser Ile Gly Gly Ala Ile Arg Thr Ala Gly Ser Tyr Leu Gly His Leu
                195                 200                 205
```

```
His Thr Gly Glu Cys Asn Arg Lys Val Pro Gly Lys Gly Arg Ile Pro
    210                 215                 220

Trp Ile Glu Ile Gly Glu Ala Leu Ala Asp Ile Gly Tyr Asn Gly Ser
225                 230                 235                 240

Val Val Met Glu Pro Phe Val Arg Met Gly Gly Thr Val Gly Ser Asn
                245                 250                 255

Ile Lys Val Trp Arg Asp Ile Ser Asn Gly Ala Asp Glu Glu Lys Leu
            260                 265                 270

Asp Arg Glu Ala Gln Ala Ala Leu Asn Phe Ser Arg Tyr Val Leu Gly
        275                 280                 285

Asn Arg Lys Leu
    290

<210> SEQ ID NO 6
<211> LENGTH: 289
<212> TYPE: PRT
<213> ORGANISM: Clostridium scindens

<400> SEQUENCE: 6

Met Lys His Gly Ile Tyr Tyr Ala Tyr Trp Glu Gln Glu Trp Ala Ala
1               5                   10                  15

Asp Tyr Lys Arg Tyr Val Glu Lys Ala Ala Lys Leu Gly Phe Asp Ile
            20                  25                  30

Leu Glu Val Gly Ala Ala Pro Leu Pro Asp Tyr Ser Ala Gln Glu Val
        35                  40                  45

Lys Glu Leu Lys Lys Cys Ala Asp Asp Asn Gly Ile Gln Leu Thr Ala
    50                  55                  60

Gly Tyr Gly Pro Ala Phe Asn His Asn Met Gly Ser Ser Asp Pro Lys
65                  70                  75                  80

Ile Arg Glu Glu Ala Leu Gln Trp Tyr Lys Arg Leu Phe Glu Val Met
                85                  90                  95

Ala Gly Leu Asp Ile His Leu Ile Gly Gly Ala Leu Tyr Ser Tyr Trp
            100                 105                 110

Pro Val Asp Phe Ala Thr Ala Asn Lys Glu Glu Asp Trp Lys His Ser
        115                 120                 125

Val Glu Gly Met Gln Ile Leu Ala Pro Ile Ala Ser Gln Tyr Gly Ile
    130                 135                 140

Asn Leu Gly Met Glu Val Leu Asn Arg Phe Glu Ser His Ile Leu Asn
145                 150                 155                 160

Thr Ser Glu Glu Gly Val Lys Phe Val Thr Glu Val Gly Met Asp Asn
                165                 170                 175

Val Lys Val Met Leu Asp Thr Phe His Met Asn Ile Glu Glu Ser Ser
            180                 185                 190

Ile Gly Asp Ala Ile Arg His Ala Gly Lys Leu Leu Gly His Phe His
        195                 200                 205

Thr Gly Glu Cys Asn Arg Met Val Pro Gly Lys Gly Arg Thr Pro Trp
    210                 215                 220

Arg Glu Ile Gly Asp Ala Leu Arg Glu Ile Glu Tyr Asp Gly Thr Val
225                 230                 235                 240

Val Met Glu Pro Phe Val Arg Met Gly Gly Gln Val Gly Ser Asp Ile
                245                 250                 255

Lys Val Trp Arg Asp Ile Ser Lys Gly Ala Gly Glu Asp Arg Leu Asp
            260                 265                 270

Glu Asp Ala Arg Arg Ala Val Glu Phe Gln Arg Tyr Met Leu Glu Trp
        275                 280                 285
```

Lys

<210> SEQ ID NO 7
<211> LENGTH: 289
<212> TYPE: PRT
<213> ORGANISM: Agrobacterium tumefaciens

<400> SEQUENCE: 7

```
Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Ile Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
                100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly
```

<210> SEQ ID NO 8
<211> LENGTH: 291
<212> TYPE: PRT
<213> ORGANISM: Ruminococcus sp.

<400> SEQUENCE: 8

```
Met Lys Tyr Gly Ile Tyr Tyr Ala Tyr Trp Glu Lys Glu Trp Asn Gly
1               5                   10                  15

Asp Tyr Lys Tyr Tyr Ile Asp Lys Ile Ser Lys Leu Gly Phe Asp Ile
```

```
            20                  25                  30
Leu Glu Ile Ser Cys Gly Ala Phe Ser Asp Tyr Tyr Thr Lys Asp Gln
        35                  40                  45

Glu Leu Ile Asp Ile Gly Lys Tyr Ala Lys Glu Lys Gly Val Thr Leu
    50                  55                  60

Thr Ala Gly Tyr Gly Pro His Phe Asn Glu Ser Leu Ser Ser Ser Glu
65                  70                  75                  80

Pro Asn Thr Gln Lys Gln Ala Ile Ser Phe Trp Lys Glu Thr Leu Arg
                85                  90                  95

Lys Leu Lys Leu Met Asp Ile His Ile Val Gly Gly Ala Leu Tyr Gly
            100                 105                 110

Tyr Trp Pro Val Asp Tyr Ser Lys Pro Phe Asp Lys Arg Asp Leu
        115                 120                 125

Glu Asn Ser Ile Lys Asn Met Lys Ile Ile Ser Gln Tyr Ala Glu Glu
    130                 135                 140

Tyr Asp Ile Met Met Gly Met Glu Val Leu Asn Arg Phe Glu Gly Tyr
145                 150                 155                 160

Met Leu Asn Thr Cys Asp Glu Ala Leu Ala Tyr Val Glu Glu Val Gly
                165                 170                 175

Ser Ser Asn Val Gly Val Met Leu Asp Thr Phe His Met Asn Ile Glu
            180                 185                 190

Glu Asp Asn Ile Ala Ala Ala Ile Arg Lys Ala Gly Asp Arg Leu Tyr
        195                 200                 205

His Phe His Ile Gly Glu Gly Asn Arg Lys Val Pro Gly Lys Gly Met
    210                 215                 220

Leu Pro Trp Asn Glu Ile Gly Gln Ala Leu Arg Asp Ile Asn Tyr Gln
225                 230                 235                 240

His Ala Ala Val Met Glu Pro Phe Val Met Gln Gly Gly Thr Val Gly
                245                 250                 255

His Asp Ile Lys Ile Trp Arg Asp Ile Ile Gly Asn Cys Ser Glu Val
            260                 265                 270

Thr Leu Asp Met Asp Ala Gln Ser Ala Leu His Phe Val Lys His Val
        275                 280                 285

Phe Glu Val
    290

<210> SEQ ID NO 9
<211> LENGTH: 301
<212> TYPE: PRT
<213> ORGANISM: Clostridium bolteae

<400> SEQUENCE: 9

Met Arg Tyr Phe Lys Glu Glu Val Ala Gly Met Lys Tyr Gly Ile Tyr
1               5                   10                  15

Phe Ala Tyr Trp Thr Lys Glu Trp Phe Ala Asp Tyr Lys Lys Tyr Met
            20                  25                  30

Asp Lys Val Ser Ala Leu Gly Phe Asp Val Leu Glu Ile Ser Cys Ala
        35                  40                  45

Ala Leu Arg Asp Val Tyr Thr Thr Lys Glu Gln Leu Ile Glu Leu Arg
    50                  55                  60

Glu Tyr Ala Lys Glu Lys Gly Leu Val Leu Thr Ala Gly Tyr Gly Pro
65                  70                  75                  80

Thr Lys Ala Glu Asn Leu Cys Ser Glu Asp Pro Glu Ala Val Arg Arg
                85                  90                  95
```

```
Ala Met Thr Phe Phe Lys Asp Leu Leu Pro Lys Leu Gln Leu Met Asp
            100                 105                 110

Ile His Ile Leu Gly Gly Gly Leu Tyr Ser Tyr Trp Pro Val Asp Phe
            115                 120                 125

Thr Ile Asn Asn Asp Lys Gln Gly Asp Arg Ala Arg Ala Val Arg Asn
        130                 135                 140

Leu Arg Glu Leu Ser Lys Thr Ala Glu Glu Cys Asp Val Val Leu Gly
145                 150                 155                 160

Met Glu Val Leu Asn Arg Tyr Glu Gly Tyr Ile Leu Asn Thr Cys Glu
                165                 170                 175

Glu Ala Ile Asp Phe Val Asp Glu Ile Gly Ser Ser His Val Lys Ile
            180                 185                 190

Met Leu Asp Thr Phe His Met Asn Ile Glu Glu Thr Asn Met Ala Asp
        195                 200                 205

Ala Ile Arg Lys Ala Gly Asp Arg Leu Gly His Leu His Leu Gly Glu
210                 215                 220

Gln Asn Arg Leu Val Pro Gly Lys Gly Ser Leu Pro Trp Ala Glu Ile
225                 230                 235                 240

Gly Gln Ala Leu Arg Asp Ile Asn Tyr Gln Gly Ala Ala Val Met Glu
                245                 250                 255

Pro Phe Val Met Gln Gly Gly Thr Ile Gly Ser Glu Ile Lys Val Trp
            260                 265                 270

Arg Asp Met Val Pro Asp Leu Ser Glu Glu Ala Leu Asp Arg Asp Ala
        275                 280                 285

Lys Gly Ala Leu Glu Phe Cys Arg His Val Phe Gly Ile
290                 295                 300

<210> SEQ ID NO 10
<211> LENGTH: 290
<212> TYPE: PRT
<213> ORGANISM: Pseudomonas cichorii

<400> SEQUENCE: 10

Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Asp Leu Gly Leu Thr Val Met
50                  55                  60

Cys Cys Ile Gly Leu Lys Ser Glu Tyr Asp Phe Ala Ser Pro Asp Lys
65                  70                  75                  80

Ser Val Arg Asp Ala Gly Thr Glu Tyr Val Lys Arg Leu Leu Asp Asp
                85                  90                  95

Cys His Leu Leu Gly Ala Pro Val Phe Ala Gly Leu Thr Phe Cys Ala
            100                 105                 110

Trp Pro Gln Ser Pro Pro Leu Asp Met Lys Asp Lys Arg Pro Tyr Val
        115                 120                 125

Asp Arg Ala Ile Glu Ser Val Arg Arg Val Ile Lys Val Ala Glu Asp
        130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
                165                 170                 175
```

```
Ser Pro Ala Cys Lys Val Gln Leu Asp Thr Phe His Met Asn Ile Glu
            180                 185                 190

Glu Thr Ser Phe Arg Asp Ala Ile Leu Ala Cys Lys Gly Lys Met Gly
            195                 200                 205

His Phe His Leu Gly Glu Ala Asn Arg Leu Pro Pro Gly Glu Gly Arg
210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Arg Ser Leu Gln Phe Val Arg Asp Lys
            275                 280                 285

Leu Ala
    290

<210> SEQ ID NO 11
<211> LENGTH: 295
<212> TYPE: PRT
<213> ORGANISM: Rhodobacter sphaeroides

<400> SEQUENCE: 11

Met Lys Asn Pro Val Gly Ile Ile Ser Met Gln Phe Ile Arg Pro Phe
1               5                   10                  15

Thr Ser Glu Ser Leu His Phe Leu Lys Lys Ser Arg Ala Leu Gly Phe
            20                  25                  30

Asp Phe Ile Glu Leu Leu Val Pro Glu Pro Glu Asp Gly Leu Asp Ala
            35                  40                  45

Ala Glu Val Arg Arg Ile Cys Glu Gly Glu Gly Leu Gly Leu Val Leu
50                  55                  60

Ala Ala Arg Val Asn Leu Gln Arg Ser Ile Ala Ser Glu Glu Ala Ala
65                  70                  75                  80

Ala Arg Ala Gly Gly Arg Asp Tyr Leu Lys Tyr Cys Ile Glu Ala Ala
                85                  90                  95

Glu Ala Leu Gly Ala Thr Ile Val Gly Gly Pro Leu Tyr Gly Glu Pro
            100                 105                 110

Leu Val Phe Ala Gly Arg Pro Pro Phe Pro Trp Thr Ala Glu Gln Ile
            115                 120                 125

Ala Thr Arg Ala Ala Arg Thr Val Glu Gly Leu Ala Glu Val Ala Pro
            130                 135                 140

Leu Ala Ala Ser Ala Gly Lys Val Phe Gly Leu Glu Pro Leu Asn Arg
145                 150                 155                 160

Phe Glu Thr Asp Ile Val Asn Thr Thr Ala Gln Ala Ile Glu Val Val
                165                 170                 175

Asp Ala Val Gly Ser Pro Gly Leu Gly Val Met Leu Asp Thr Phe His
            180                 185                 190

Met Asn Met Glu Glu Arg Ser Ile Pro Asp Ala Ile Arg Ala Thr Gly
            195                 200                 205

Ala Arg Leu Val His Phe Gln Ala Asn Glu Asn His Arg Gly Phe Pro
            210                 215                 220

Gly Thr Gly Thr Met Asp Trp Thr Ala Ile Ala Arg Ala Leu Gly Gln
225                 230                 235                 240

Ala Gly Tyr Ala Gly Pro Val Ser Leu Glu Pro Phe Arg Arg Asp Asp
```

```
                         245                 250                 255
Glu Arg Val Ala Leu Pro Ile Ala His Trp Arg Ala Pro His Glu Asp
        260                 265                 270

Glu Asp Glu Lys Leu Arg Ala Gly Leu Gly Leu Ile Arg Ser Ala Ile
    275                 280                 285

Thr Leu Ala Glu Val Thr His
    290                 295

<210> SEQ ID NO 12
<211> LENGTH: 27
<212> TYPE: DNA
<213> ORGANISM: artificial sequence
<220> FEATURE:
<223> OTHER INFORMATION: primer

<400> SEQUENCE: 12
catttacaca ctagcgaatg taatcgt                                       27

<210> SEQ ID NO 13
<211> LENGTH: 27
<212> TYPE: DNA
<213> ORGANISM: artificial sequence
<220> FEATURE:
<223> OTHER INFORMATION: primer

<400> SEQUENCE: 13
catttacaca ctgccgaatg taatcgt                                       27

<210> SEQ ID NO 14
<211> LENGTH: 27
<212> TYPE: DNA
<213> ORGANISM: artificial sequence
<220> FEATURE:
<223> OTHER INFORMATION: primer

<400> SEQUENCE: 14
catttacaca ctgacgaatg taatcgt                                       27

<210> SEQ ID NO 15
<211> LENGTH: 27
<212> TYPE: DNA
<213> ORGANISM: artificial sequence
<220> FEATURE:
<223> OTHER INFORMATION: primer

<400> SEQUENCE: 15
catttacaca ctcgcgaatg taatcgt                                       27

<210> SEQ ID NO 16
<211> LENGTH: 27
<212> TYPE: DNA
<213> ORGANISM: artificial sequence
<220> FEATURE:
<223> OTHER INFORMATION: primer

<400> SEQUENCE: 16
catttacaca cttgggaatg taatcgt                                       27

<210> SEQ ID NO 17
<211> LENGTH: 27
<212> TYPE: DNA
<213> ORGANISM: artificial sequence
<220> FEATURE:
<223> OTHER INFORMATION: primer
```

```
<400> SEQUENCE: 17
catttacaca ctctcgaatg taatcgt                                          27

<210> SEQ ID NO 18
<211> LENGTH: 30
<212> TYPE: DNA
<213> ORGANISM: artificial sequence
<220> FEATURE:
<223> OTHER INFORMATION: primer

<400> SEQUENCE: 18
agtgtgtaaa tgtcccaagt aagagcccgc                                       30

<210> SEQ ID NO 19
<211> LENGTH: 29
<212> TYPE: DNA
<213> ORGANISM: artificial sequence
<220> FEATURE:
<223> OTHER INFORMATION: primer

<400> SEQUENCE: 19
cgccatatga aacatggtat atactacgc                                        29

<210> SEQ ID NO 20
<211> LENGTH: 25
<212> TYPE: DNA
<213> ORGANISM: artificial sequence
<220> FEATURE:
<223> OTHER INFORMATION: primer

<400> SEQUENCE: 20
cgcggatcct tgttagccgg atctc                                            25
```

VARIANT OF D-PSICOSE 3-EPIMERASE AND USES THEREOF

CROSS-REFERENCE TO RELATED APPLICATION

This application is a divisional of application Ser. No. 14/914,264 filed on Feb. 25, 2016, now U.S. Pat. No. 9,790,481, issued Oct. 17, 2017, which is the U.S. national stage application of International Patent Application No. PCT/EP2014/068628, filed Sep. 2, 2014. The entire contents of these applications are incorporated herein by reference in their entirety.

SEQUENCE LISTING

The instant application contains a Sequence Listing which has been filed electronically in ASCII format and is hereby incorporated by reference in its entirety. Said ASCII copy, created on Nov. 14, 2017, is named 20058800245SL.txt and is 33,474 bytes in size.

FIELD OF THE INVENTION

The present invention relates to an improved isomerase, in particular D-psicose-3-epimerase, for preparing psicose from fructose and its uses.

BACKGROUND OF THE INVENTION

D-psicose, also called D-allulose, is a rare sugar isomer of fructose. It can be found in nature but at very low concentrations like in edible mushrooms, jackfruit, wheat and the Itea plants.

Unlike fructose, the metabolism of psicose in humans is partly absorbed and metabolized in energy, and partly excreted unchanged in the urine and feces.

The characteristics of D-psicose as a material for preventing lifestyle-related diseases have been disclosed, including its noncaloric nature, a positive effect on the reduction of the glycemic response, an antiobesity effect, and the like. In addition, the sweetness of D-psicose is about 70% of that of sucrose (Oshima, et al. (2006), Psicose contents in various food products and its origin, *Food Sci Technol Res* 12:137-143), but 0.3% energy of sucrose and is suggested as an ideal sucrose substitute for food products. It can also be used as an inhibitor of hepatic lipogenic enzyme and intestinal α-glycosidase for reducing body fat accumulation. It further shows important physiological functions, such as reactive oxygen species scavenging activity and a neuroprotective effect. In addition, it also improves the gelling behavior and produces good flavor during food processing.

D-psicose exists in extremely small quantities in commercial carbohydrate or agricultural products and is difficult to chemically synthesize. Therefore, interconversion between D-fructose and D-psicose by epimerization using D-tagatose 3-epimerase (DTEase) family enzymes has been confused on as attractive way of D-psicose production.

So far, there have been 9 kinds of DTEase family enzyme sources reported. Twenty years ago, DTEase was first characterized by Izumori et al, from *Pseudomonas cichorii*, showing C-3 epimerization activity of ketohexoses with the optimum substrate of D-tagatose (Izumori et al. 1993, *Biosci, Biotechnol, Biochem,* 57, 1037-1039). Till 2006, the second enzyme with C-3 epimerization activity of ketohexoses was identified from *Agrobacterium tumefaciens*, and it was named D-psicose 3-epimerase (DPEase), due to its high substrate specificity for D-psicose (Kim et al. 2006, *Applied and environmental microbiology* 72, 981-985; US 2010/0190225; WO2011/040708). Recently, another six DTEase family enzymes were characterized from *Rhodobacter sphaeroides* SK011 (DTEase) (Zhang et al. 2009, *Biotechnology letters* 31, 857-862), *Clostridium cellulolyticum* H10 (DPEase) (Mu et al. 2011, *Journal of agricultural and food, chemistry* 59, 7785-7792, CN102373230), *Ruminococcus* sp. 5_1_39BFAA (DPEase) (Zhu et al, 2012, *Biotechnology letters* 34, 1901-1906), *Clostridium bolteae* ATCC BAA-613 (Jia et al. 2013, *Applied Microbiology and Biotechnology, DOI* 10.1007/s00253-013-4924-8), *Clostridium scindens* ATCC 35704 (Zhang et al. 2013, *PLoS ONE* 8, e62987), and *Clostridium* sp. BNL1100 (Mu et al. 2013, *Biotechnology Letters, DOI* 10.1007/s10529-013-1230-6), respectively. In addition, Maruta et al. disclosed a DTEase-producing source in *Rhizobium* (US 2011/0275138).

There is only one reference to report the enzyme modification of DTEase family enzymes by protein engineering technology. Using random and site-directed mutagenesis technology, Choi et al. (2011, *Applied and environmental microbiology* 77, 7316-7320) constructed the I33L S213C double-site variant of *A. tumefaciens* DPEase, and the variant enzyme showed increases in optimal temperature, half-life, melting temperature, and catalysis efficiency, compared with the wild-type enzyme. Its optimal pH remains unchanged at 8.00.

However, the enzymes have optimum pH for activity at 8.0-9.5, and the pH stability is between 8.0-10.0, which is not appropriate for industrial application.

Therefore, the main concern for using psicose remains its scarcity and its production cost, and the need for improved industrial D-psicose production still exists.

SUMMARY OF THE INVENTION

To develop industrial D-psicose production and reduce the production cost, an optimized DTEase family enzyme should be weak-acid stable and thermostable, and have a higher catalysis efficiency and turnover for the substrate D-fructose.

The present invention relates to a variant of a parent D-psicose 3-epimerase, wherein the variant comprises a substitution of a glycine residue by a serine residue at a position corresponding to position 211 in SEQ ID NO: 2 compared to the parent D-psicose 3-epimerase, and wherein the variant has a D-psicose 3-epimerase activity. Preferably, the parent D-psicose 3-epimerase having an amino acid sequence having 60% identity or higher with a sequence selected from the group consisting of SEQ ID NOs: 2 and 5-10, more preferably 70, 75, 80, 85, 90, 95 or 99% identity or higher with a sequence selected from the group consisting of SEQ ID NOs: 2 and 5-10.

In a preferred embodiment, the variant has one or several following features:
 a. a lower pH optimum compared to the parent D-psicose 3-epimerase, preferably in the range of 6 to 7; and/or
 b. a higher catalysis efficiency to the substrate D-fructose compared to the parent-psicose 3-epimerase, preferably at least twice as high; and/or
 c. a longer half-life at 60° C. compared to the parent-psicose 3-epimerase.

Preferably, the variant has an amino acid sequence having 35% identity or higher with SEQ ID NO: 2, preferably 60% identity or higher, more preferably at least 70, 75, 80, 85, 90, or 95% identity or higher.

Preferably, the variant has an amino acid sequence having 60% identity or higher with a sequence selected from the group consisting of SEQ ID NOs: 2 and 5-10, more preferably at least 70, 75, 80, 85, 90, or 95% identity or higher with a sequence selected from the group consisting of SEQ ID NOs: 2 and 5-10.

In a preferred embodiment, the parent D-psicose 3-epimerase is selected from a D-tagatose 3-epimerase from *Pseudomonas cichorii*, a D-psicose 3-epimerase from *Agrobacterium tumefaciens*, a D-psicose 3-epimerase from *Clostridium* sp., a D-psicose 3-epimerase from *Clostridium scindens*, a D-psicose 3-epimerase from *Clostridium bolteae*, a D-psicose 3-epimerase from *Ruminococcus* sp., and a D-psicose 3-epimerase from *Clostridium cellulolyticum*. More preferably, the parent D-psicose 3-epimerase is the D-psicose 3-epimerase from *Clostridium cellulolyticum*.

In a most preferred embodiment, the variant comprises or consists of the amino acid sequence of SEQ ID NO: 4 or an amino acid sequence having 90 or 95% identity or higher with SEQ ID NO: 4 and having a residue serine at position 211.

In an alternative preferred embodiment, the variant comprises or consists of:
the amino acid sequence of SEQ ID NO: 5 with a G211S substitution or an amino acid sequence having 90 or 95% identity or higher with SEQ ID NO: 5 and having a residue Ser at position 211; or
the amino acid sequence of SEQ ID NO: 6 with a G210S substitution or an amino acid sequence having 90 or 95% identity or higher with SEQ ID NO: 6 and having a residue Ser at position 210; or
the amino acid sequence of SEQ ED NO: 7 with a G211S substitution or an amino acid sequence having 90 or 95% identity or higher with SEQ ID NO: 7 and having a residue Ser at position 211; or
the amino acid sequence of SEQ ED NO: 8 with a G213S substitution or an amino acid sequence having 90 or 95% identity or higher with SEQ ID NO: 8 and having a residue Ser at position 213; or
the amino acid sequence of SEQ ED NO: 9 with a G223S substitution or an amino acid sequence having 90 or 95% identity or higher with SEQ ID NO: 7 and having a residue Ser at position 223; or
the amino acid sequence of SEQ ID NO: 10 with a G213S substitution or an amino acid sequence having 90 or 95% identity or higher with SEQ ED NO: 10 and having a residue Ser at position 213.

Another object of the present invention is an isolated nucleic acid encoding a variant according to the present invention. The present invention further relates to an expression cassette or recombinant expression vector comprising a nucleic acid encoding a variant according to the present invention. It also relates to a recombinant host cell comprising a nucleic acid according to the present invention, an expression cassette according to the present invention or a recombinant expression vector according to the present invention. Preferably, the nucleic acid encoding the variant according to the present invention is integrated into the host cell's chromosome. In a particular embodiment, the host cell is a GRAS strain (Generally Recognized As Safe), preferably *Bacillus subtilis*. In some embodiments, the recombinant host cell is a *Bacillus subtilis* strain wherein the gene encoding for bacillopeptidase F is inactivated.

The present invention relates to a method for producing a D-psicose 3-epimerase variant comprising culturing the recombinant host cell according to the present invention, and optionally recovering or purifying the produced D-psicose 3-epimerase variant from the resulting culture. In other word, it relates to the use of a recombinant host cell according to the present invention for producing a D-psicose 3-epimerase variant according to the present invention.

The present invention also relates to a method for producing D-psicose comprising contacting a variant according to the present invention with D-fructose in conditions suitable for the D-psicose 3-epimerase activity and optionally recovering the produced D-psicose. Optionally, the D-fructose is previously or simultaneously produced by a glucose isomerase from D-glucose. Thus, the present invention relates to the use of a D-psicose 3-epimerase variant according to the present invention or a recombinant host cell according to the present invention for producing D-psicose.

An object of the present invention is an enzymatic composition comprising a D-psicose 3-epimerase variant according to the present invention and an additional enzyme, in particular a glucose isomerase.

Finally, the present invention relates to the use of a GRAS host cell according to the present invention for preparing a food product and to a food product comprising such a GRAS host cell.

DETAILED DESCRIPTION OF THE INVENTION

The present invention relates to an improved variant of a D-psicose 3-epimerase.

Definitions

In the present document, the term "DPEase" and "DTEase" could be used in place of "D-psicose 3-epimerase" and "D-tagatose 3-epimerase", respectively, "DPEase" and "DTEase" mean the ketose 3-epimerases with the optimum substrates as D-psicose and D-tagatose, respectively.

The term "parent" means an enzyme to which an alteration is made to produce the variants of the present invention. The parent may be a naturally occurring (wild-type) polypeptide or a variant or fragment thereof. In a preferred embodiment, the parent D-psicose 3-epimerase is one selected from those shown in SEQ ID NOs: 2 and 5-10.

In addition, the term "DPEase variant" may also refer to a variant of a D-tagatose 3-epimerase as taught in the present invention.

Identity Percentage: The "percentage identity" between two amino acid sequences (A) and (B) is determined by comparing the two sequences aligned in an optimal manner, through a window of comparison. Said alignment of sequences can be carried out by well-known methods, for example, using the algorithm for global alignment of Needleman-Wunsch.

Protein analysis software matches similar sequences using measures of similarity assigned to various substitutions, deletions and other modifications, including conservative amino acid substitutions. Once the total alignment is obtained, the percentage of identity can be obtained by dividing the full number of identical amino acid residues aligned by the full number of residues contained in the longest sequence between sequences (A) and (B). Sequence identity is typically determined using sequence analysis software. For comparing two amino acid sequences, one can use, for example, the tool "Emboss needle" for pairwise sequence alignment of proteins providing by EMBL-EBI and available on Worldwide Website: ebi.ac.uk/Tools/services/web/tool form.ebi?tool=emboss_needle&context=protein, using default settings: (I) Matrix: BLOSUM62, (ii) Gap open: 10, (iii) gap extend: 0.5, (iv) output format: pair, (v) end gap penalty: false, (vi) end gap open: 10, and (vii) end gap extend: 0.5.

By "about" is intended the value more or less 10% of the value. Preferably, it is intended the value more or less 5% of the value. For instance, "about 100" means between 90 and 110, preferably between 95 and 105.

By "D-psicose 3-epimerase activity" is referred the capacity of the enzyme to modify D-fructose into D-psicose. This activity can be assayed by measuring the amount of D-psicose formed from D-fructose. In particular, it can be measured as detailed in the Examples section or as disclosed in Mu et al. (2011, *Journal of agricultural and food chemistry* 59, 7785-7792, in the "Enzyme Assay" section, page 7787).

Variant of D-psicose 3-epimerase

The present invention relates to a variant of a parent D-psicose 3-epimerase, wherein the variant comprises a substitution of a glycine residue by a serine residue at a position corresponding to position 211 in SEQ ID NO: 2 compared to the parent D-psicose 3-epimerase, and wherein the variant has a D-psicose 3-epimerase activity.

Preferably, the parent D-psicose 3-epimerase has an amino acid sequence having 60% identity or higher with a sequence selected from the group consisting of SEQ ID NOs: 2 and 5-10. In particular, the parent may have an amino acid sequence having at least 70, 75, 80, 85, 90 or 95% identity or higher with a sequence selected from the group consisting of SEQ ID NOs: 2 and 5-10.

The inventors surprisingly identified a G211S variant of DPEase from *C. cellulolyticum* as an improved variant. Indeed, this variant presents the following advantages (see Tables 1 and 2):
  a lower pH optimum, namely 6.5 instead of 8.0 for the wild-type DPEase;
  a higher half-life at 60° C., namely 7.2 h instead of 6.8; and
  a higher $k_{cat}/K_m$ for D-fructose, namely 150.6 instead of 62.7.

According to the knowledge of the inventors, it is the first time that a DPEase is reported with a pH optimum lower than 7.0. In addition, the lowering of the pH optimum goes along with an improved stability and a strong increase of catalytic efficiency.

Accordingly, the DPEase variant has one or several following features:
  a. a lower pH optimum compared to the parent D-psicose 3-epimerase, preferably in the range of 6 to 7; and/or
  b. a higher catalysis efficiency to the substrate D-fructose compared to the parent-psicose 3-epimerase, preferably at least 50, 75, 100, or 120% higher, more preferably at least twice as high; and/or
  c. a longer half-life at 60° C., preferably at least 5, 10, 15 or 20 minutes longer.

In a first embodiment, the DPEase variant fulfils the requirement of items a) and b), items a) and c), items b) and c), or items a), b) and c). Preferably, the DPEase variant has a lower pH optimum compared to the parent D-psicose 3-epimerase, preferably in the range of 6 to 7. Therefore, the DPEase variant fulfils the requirement of items a) and b), items a) and c), or items a), b) and c).

In addition, the variant has an amino acid sequence having 60% identity or higher with an amino acid sequence of parent D-psicose 3-epimerases selected from the group consisting of SEQ ID NOs: 2 and 5-10. In particular, the variant has an amino acid sequence having at least 70, 75, 80, 85, 90 or 95% identity or higher with a sequence selected from the group consisting of SEQ ID NOs: 2 and 5-10.

In a particular embodiment, the variant comprises a substitution of a glycine residue by a serine residue at a position corresponding to position 211 in SEQ ID NO: 2 of the parent D-psicose 3-epimerase, has a D-psicose 3-epimerase activity, and has at least 60, 70, 75, 80, 85, 90 or 95% identity or higher with a sequence selected from the group consisting of SEQ ID NO: 2 and 5-10. In addition, the variant can fulfil the requirement of items a) and b), items a) and c), items b) and c), or items a), b) and c) as disclosed above.

The inventors further noted that, despite a quite low amino acid (aa) sequence identity between D-tagatose 3-epimerase from *Pseudomonas cichorii*, D-psicose 3-epimerase from *Agrobacterium tumefaciens*, and D-psicose 3-epimerase from *Clostridium cellulolyticum* (i.e., DTEase of *P. cichorii* has 41% aa identity with DPEase of *C. cellulolyticum*; DPEase of *A. tumefaciens* has 60% aa identity with DPEase of *C. cellulolyticum*), the residue G211 of the DPEase of *C. cellulolyticum* is conserved. Furthermore, as shown in FIG. 1, G211 is conserved in seven of the eight enzymes (see FIG. 1).

Then, the present invention relates to a DPEase variant having an amino acid sequence having 35% identity or higher with SEQ ID NO: 2, preferably 60% identity or higher, more preferably at least 70, 75, 80, 85, 90, or 95% identity or higher. It is obviously understood that all the DPEase variants of the present invention present the substitution of Gly by Ser at the position corresponding to residue 211 in SEQ ID NO: 2.

More particularly, the parent D-psicose 3-epimerase is selected from a D-tagatose 3-epimerase from *Pseudomonas cichorii*, a D-psicose 3-epimerase from *Agrobacterium tumefaciens*, a D-psicose 3-epimerase from *Clostridium* sp., a D-psicose 3-epimerase from *Clostridium scindens*, a D-psicose 3-epimerase from *Clostridium bolteae*, a D-psicose 3-epimerase from *Ruminococcus* sp., and a D-psicose 3-epimerase from *Clostridium cellulolyticum*. In a preferred embodiment, the parent D-psicose 3-epimerase is a D-psicose 3-epimerase from *Clostridium cellulolyticum*, more particularly *Clostridium cellulolyticum* strain H10 (ATCC 35319).

Therefore, the present invention relates to a DPEase variant having or comprising the amino acid sequence of SEQ ID NO: 2 with a G211S substitution (i.e., the amino acid sequence of SEQ ID NO: 4) or an amino acid sequence having 90 or 95% identity or higher with SEQ ID NO: 4 and having a residue Ser at position 211.

Alternatively, it also relates to a DPEase variant having or comprising the amino acid sequence of SEQ ID NO: 5 with a G211S substitution or an amino acid sequence having 90 or 95% identity or higher with SEQ ID NO: 5 and having a residue Ser at position 211.

In addition, it also relates to a DPEase variant having or comprising the amino acid sequence of SEQ ID NO: 6 with a G210S substitution or an amino acid sequence having 90 or 95% identity or higher with SEQ ID NO: 6 and having a residue Ser at position 210.

Alternatively, it also relates to a DPEase variant having or comprising the amino acid sequence of SEQ ID NO: 7 with a G211S substitution or an amino acid sequence having 90 or 95% identity or higher with SEQ ID NO: 7 and having a residue Ser at position 211.

In addition, it also relates to a DPEase variant having or comprising the amino acid sequence of SEQ ID NO: 8 with a G213S substitution or an amino acid sequence having 90 or 95% identity or higher with SEQ ID NO: 8 and having a residue Ser at position 213, Alternatively, it also relates to a DPEase variant having or comprising the amino acid sequence of SEQ ID NO: 9 with a G223S substitution or an amino acid sequence having 90 or 95% identity or higher with SEQ ID NO: 7 and having a residue Ser at position 223.

Finally, it also relates to a DTEase variant having or comprising the amino acid sequence of SEQ ID NO: 10 with a G213S substitution or an amino acid sequence having 90 or 95% identity or higher with SEQ ID NO: 10 and having a residue Ser at position 213.

Optionally, the variant has alterations at not more than 11, 10, 9, 8, 7, 6, 5, 4, 3, 2 or 1 amino acids, e.g., may have substitutions, insertions, and/or deletions of 1, 2, 3, 4, 5, 6, 7, 8, 9 or 10 amino acids.

The present invention also relates to a DPEase variant according to the present invention further comprising a tag. For instance, it can comprise a tag suitable for facilitating the DPEase variant purification or immobilization, such as a His tag (His$_6$), a FLAG tag, an HA tag (epitope derived from the influenza protein hemagglutinin), a MYC tag (epitope derived from the human proto-oncoprotein MYC) or a GST tag (small glutathione-S-transferase).

Finally, the present invention relates to a DPEase variant according to the present invention immobilized on a solid support or a carrier. The DPEase can be immobilized on any suitable support or carrier, such as alginate, amberlite resin, Sephadex resin or Duolite resin, e.g., beads. Immobilization means are well-known to the person skilled in the art. For instance, see Choi et al, supra; Lim et al. (2009, *Process Biochemistry* 44, 822-828); and WO2011/040708, the disclosures thereof being incorporated herein by reference.

Nucleic Acid, Vector and Host Cells

The present invention relates to a nucleic acid encoding a DPEase variant according to the present invention or a nucleic acid comprising a sequence encoding a DPEase variant according to the present invention. The present invention also relates to an expression cassette of a nucleic acid according to the invention. It further relates to a vector comprising a nucleic acid or an expression cassette according to the invention. Preferably, the vector is an expression vector. The vector is preferably a plasmid vector. In addition, the present invention relates to a host cell comprising a nucleic acid according to the invention, an expression cassette of a nucleic acid according to the invention or a vector comprising a nucleic acid or an expression cassette according to the invention. The nucleic acid encoding a DPEase variant according to the present invention can be present in the host cell as an episomic sequence or can be incorporated into its chromosome. The nucleic acid encoding a DPEase variant according to the present invention can be present in the host cell in one copy or in several copies.

The nucleic acid can be DNA (cDNA or gDNA), RNA, or a mixture of the two. It can be in single-stranded form or in duplex form or a mixture of the two. It can comprise modified nucleotides, for example a modified bond, a modified purine or pyrimidine base, or a modified sugar. It can be prepared by any method known to one skilled in the art, including chemical synthesis, recombination, mutagenesis, etc.

The expression cassette comprises all elements required for expression of the DPEase variant according to the present invention, in particular the elements required for transcription and translation in the host cell, in particular in the considered host cell.

The host cell can be prokaryotic or eukaryotic, preferably prokaryotic or lower eukaryotic, more preferably prokaryotic. In particular, the expression cassette comprises a promoter and a terminator, and optionally an enhancer. The promoter can be prokaryotic or eukaryotic, depending on the selected host cell. Examples of preferred prokaryotic promoters include Lacl, LacZ, pLacT, ptac, pARA, pBAD, the RNA polymerase promoters of bacteriophage T3 or T7, the polyhedrin promoter, and the PR or PL promoter of lambda phage. In general, to select a suitable promoter, one skilled in the art may advantageously consult Sambrook et al. (1989) or techniques described by Fuller et al. (1996, *Immunology in Current Protocols in Molecular Biology*). In a preferred embodiment, a strong promoter is operationally linked to the coding sequence of the DPEase variant.

The present invention relates to a vector containing a nucleic acid or an expression cassette encoding the DPEase variant according to the present invention. The vector is preferably an expression vector, that is to say, it comprises the elements required for the expression of the variant in the host cell. The vector is a self-replicable vector. The host cell can be a prokaryote, for example *E. coli*, or a eukaryote. The eukaryote can be a lower eukaryote such as a yeast (for example, *S. cerevisiae*) or fungus (for example from the genus *Aspergillus* or *Actinomyces*) or a higher eukaryote such as an insect, mammalian or plant cell. The cell can be a mammalian cell, for example COS, CHO (U.S. Pat. Nos. 4,889,803; 5,047,335). In a particular embodiment, the cell is non-human and non-embryonic.

The vector can be a plasmid, phage, phagemid, cosmid, virus, YAC, BAC, pTi plasmid from *Agrobacterium*, etc. The vector can preferably comprise one or more elements selected from the group consisting of a replication origin, a multiple cloning site and a selection gene. In a preferred embodiment, the vector is a plasmid. The vector is a self-replicable vector. Examples of prokaryotic vectors include, but are not limited to, the following: pER322, pQE70, pMA5, pUC18, pQE60, pUB110, pQE-9 (Qiagen), pbs, pTZ4, pC194, pD10, pHV14, Yep7, phagescript, psiX174, pbluescript SK, pbsks, pNH8A, pNH16A, pNH18A, pNH46A (Stratagene), ptrc99a, pKK223-3, pKKC233-3, pDR540, pBR322, pRIT5 (Pharmacia), and pET (Novagen). Examples of eukaryotic vectors include, but are not limited to, the following: pWLNEO, pSV2CAT, pPICZ, pcDNA3.1 (+) Hyg (Invitrogen), pOG44, pXT1, pSG (Stratagene), pSVK3, pBPV, pCI-neo (Stratagene), pMSG, pSVL (Pharmacia), and pQE-30 (QLAexpress). Preferably the expression vector is a plasmid vector.

More particularly, to express in *E. coli*, pBR322, pUC18, pBluescript II SK (+), λgt. λC and λgt. λB can be preferably used, while to express in *Bacillus subtilis*, pUB110, pTZ4, pC194, pi 1, Φ1 and Φ105 can be preferably used. Plasmids, pHV14, TRp7, YEp7 and pBS7 are useful in the case of replicating the recombinant nucleic acid in two or more kinds of hosts. In order to insert an encoding nucleic acid sequence into these vectors, conventional methods in the art can be used.

In a particular embodiment, the vector is an integration vector suitable to incorporate the sequence encoding the DPEase variant according to the present invention into the chromosome of the host cell. A non-exhaustive example of commercially available integration vectors is pMUTIN4 for *B. subtilis* from the *Bacillus* Genetic Stock Center.

Accordingly, in a preferred aspect, the invention relates to a host cell having a nucleic acid encoding the DPEase variant according to the present invention integrated into its chromosome. The host cell's chromosome can include one or several copies of the nucleic acid encoding the DPEase variant (e.g., 2, 3, 4 or 5 copies). Said nucleic acid can be introduced by any method known in the art, for instance by homologous recombination or random integration. In a preferred embodiment, the nucleic acid encoding the DPEase variant is introduced by the Cre-loxP method (see Yan et al., *Appl. Environm. Microbiol.*, 2008, 74, 5556-5562) or any analogous method such as an mazF-based system. In a preferred embodiment, the host cell does not include any heterologous selection gene such as an antibiotic resistance gene. For instance, the nucleic acid encoding the DPEase variant can be first introduced into the host cell's chromosome together with a heterologous selection gene, and then the heterologous selection gene is deleted from host cell's chromosome.

The host cell can be preferably selected among the group consisting of *E. coli* and GRAS strains. Preferably, the GRAS strain is selected from the group consisting of innocuous bacteria, especially innocuous *Corynebacterium* sp. such as *C. glutamicum*, and innocuous *Bacillus* sp. such as *B. subtilis*. In a very specific embodiment, the host cell is of *E. coli* or *B. subtilis*, preferably *B. subtilis*.

In some embodiments, the host cell may be a GRAS strain in which one or several genes are inactivated or activated so as to increase the production of active DPEase by said strain.

Indeed, the inventors showed that the bacillopeptidase F, one of the proteases naturally produced in *Bacillus subtilis* strains, may exhibit a hydrolysis activity towards DPEase, which may limit the production yield of active DPEase by the host cells. Thus, in a particular embodiment, the host cell is a GRAS strain wherein at least one of the genes encoding for a protease susceptible to hydrolyze DPEase is attenuated or inactivated. As used herein, a strain exhibiting "an attenuated gene" refers to a mutated strain displaying a decrease of the expression of said gene or a decrease of the activity of the protein encoded by said gene, as compared to the corresponding wild-type strain. The methods for attenuating or inactivating genes are well-known for the skilled artisan. The attenuation of the gene may be obtained, for instance, by:

the introduction of one or several mutations into the gene, so as to decrease the expression level of the gene, or so as to alter the biological activity of the encoded protein, e.g., insertions, deletions, or random or directed mutations, for instance frameshift mutations, point mutations or insertion of stop codons; for example, in the context of the invention, the mutation may lead to the production of a protease with a very low hydrolysis activity toward DPEase;

the replacement of the natural promoter of the gene by a low strength promoter, resulting from a lower production of the protein;

the use of elements destabilizing the corresponding messenger RNA or the protein; or the deletion of the gene or a part thereof, in particular knocked-out.

In some embodiments, the host cell is a GRAS strain wherein the attenuated gene is a gene encoding for a serine endopeptidase susceptible to hydrolyzing DPEase.

In some additional embodiments, the host cell is a *Bacillus* strain, preferably a *Bacillus subtilis* strain wherein the gene encoding for bacillopeptidase F is attenuated or inactivated. In some further embodiments, the host cell is & *Bacillus subtilis* strain wherein the gene encoding for bacillopeptidase F is knocked out. Such knockout may be obtained by deleting the corresponding genomic DNA in the genome of said strain. For illustration, the gene ID for bacillopeptidase F gene (brp) in *Bacillus subtilis* is described in Sloma et al. (1990, *J Bacteriol.*, 172, 1470-1477).

The present invention relates to the use of a nucleic acid, an expression cassette, an expression vector or a host cell as disclosed above for producing a DPEase variant according to the present invention.

It also relates to a method for producing a DPEase variant according to the present invention, comprising culturing the recombinant host cell according to the present invention, and optionally recovering and/or purifying the produced D-psicose 3-epimerase variant from the resulting culture. In a preferred embodiment, the host cell is selected from *E. coli* and GRAS strains, especially *B. subtilis*.

Optionally, the host cell further produces a glucose isomerase.

In a particular embodiment, the present invention relates to an immobilized host cell according to the present invention producing and secreting a DPEase variant of the present invention.

Production of D-psicose

The present invention relates to the use of a DPEase variant according the present invention for producing D-psicose and to the method for producing D-psicose by using a DPEase variant according the present invention.

In a first embodiment, the DPEase variant is contacted with D-fructose in conditions suitable for the D-psicose 3-epimerase activity. D-fructose can be provided as high fructose syrup, and in particular high fructose corn syrup. Such high fructose corn syrups are commercially available from Roquette Freres under the HI-SWEET® references.

In another particular embodiment, D-glucose is contacted with an enzyme mixture comprising a DPEase variant according the present invention and a glucose isomerase. The glucose isomerase is also called xylose isomerase and corresponds to EC 5.3.1.5. Preferably, glucose is provided as a glucose syrup, in particular a corn syrup.

In another alternative, the starting material may be starch in place of glucose or fructose, and the enzyme mixture further comprises alpha-amylase and/or glucoamylase.

The present invention relates to an enzyme mix comprising a DPEase variant according the present invention and an additional enzyme. Preferably, the enzyme mix comprises a DPEase variant according the present invention and a glucose isomerase. Optionally, the enzyme mix may further comprise alpha-amylase and/or glucoamylase.

Suitable conditions for producing D-psicose can be defined by the person skilled in the art. Preferably, they include the following features:

temperature: between 50 and 60° C., preferably about 55° C.; and/or pH: between 5.5 and 7.5, preferably between 6 and 7, more preferably about 6.5; and/or in the presence of a divalent metal ion, preferably selected from the group consisting of $Co^{2+}$, $Mn^{2+}$, $Fe^{2+}$, $Ni^{2+}$ and $Mg^{2+}$, more preferably from $Co^{2+}$, $Mn^{2+}$, $Fe^{2+}$, and $Ni^{2+}$, still preferably from $Co^{2+}$ and $Mn^{2+}$, and most preferably $Co^{2+}$; and/or in the presence of borate when immobilized TDEase is used, e.g., 40-80 mM of borate, preferably about 60 mM.

In a particular embodiment, the enzymes to be used in the method are immobilized. More particularly, the DPEase variant of the present invention is immobilized. Optionally, both glucose isomerase and the DPEase variant of the present invention can be immobilized or solely the DPEase variant. In another alternative, instead of immobilizing the enzyme, the microorganisms producing the enzymes are immobilized. The enzyme(s) or microorganisms can be for instance immobilized on any suitable support, such as alginate, amberlite resin, Sephadex resin or Duolite resin, e.g., beads.

The immobilized enzyme(s) or microorganisms can be packed into a suitable column and the glucose or fructose liquid or syrup is continuously introduced into the column.

Methods for immobilized DPEases on a support and to produce D-psicose are well-known to the person skilled in the art, for instance in WO2011/040708.

The resulting product can be a mixture of D-fructose and D-psicose, and even a mixture of D-glucose, D-fructose and D-psicose.

An aspect of the present invention relates to the use of a GRAS host cell according to the present invention for preparing a food product and to a food product comprising such a GRAS host cell. The food products are for humans or for animal feed. For instance, the foods can be foods for health, foods for patients, food materials, food materials for health, food materials for patients, food additives, food additives for health, food additives for patients, beverages, beverages for health, beverages for patients, potable water, potable water for health, potable water for patients, drugs, drug raw materials, feeds, and feeds for diseased domestic animals and/or diseased animals. When used as a food material or a food additive, it can be used for alleviating abnormal carbohydrate metabolism and/or abnormal lipid metabolism. It may be in the form of a solid preparation such as a tablet; a capsule; a powder or granules to be dissolved in beverages, etc.; a semisolid preparation such as jelly; a liquid such as potable water; a high-concentration solution to be diluted before use; or the like.

BRIEF DESCRIPTION OF THE DRAWINGS

FIG. 1. Multiple sequence alignment of DTEase family enzymes and their homologs. Amino acid sequence were from *C. cellulolyticum* DPEase (Clce-DPEase; GeneBank Accession No: ACL75304), SEQ ID NO: 4, *Clostridium sp.* (Clsp-DPEase; YP_005149214.1), SEQ ID NO: 5, *C. scindens* DPEase (Clsc-DPEase; EDS06411.1), SEQ ID NO: 6, *A. tumefaciens* DPEase (Agtu-DPEase; AAL45544), SEQ ID NO: 7, *C. bolteae* DPEase (Clbo-DPEase; EDP19602), SEQ ID NO: 9, *Ruminococcus sp.* DPEase (Rusp-DPEase; ZP_04858451), SEQ ID NO: 8, *P. cichorii* DTEase (Psci-DTEase; BAA24429), SEQ ID NO: 10, and *R. sphaeroides* DTEase (Rhsp-DTEase; AC059490), SEQ ID NO: 11. The alignment was performed using the ClustalW2 program (World Wide Web site: ebi.ac.uk/Tools/clustalw2/index.html). Amino acid residues that are identical in all the displayed sequences are marked by asterisks (*); strongly conserved or weakly conserved residues are indicated by colons (:) or dots (.), respectively.

EXAMPLE 1

The inventors prepared, by site-directed mutagenesis, DPEase variants of *C. cellulolyticum* by replacing the codon GGC encoding Gly in position 211 (SEQ ID NO: 1) by the codons AGC, GCC, GAC, CGC, TGG and CTC, encoding respectively the substitutions G211S, G211A, G211D, G211T, G211W and G211L.

Figure 3:
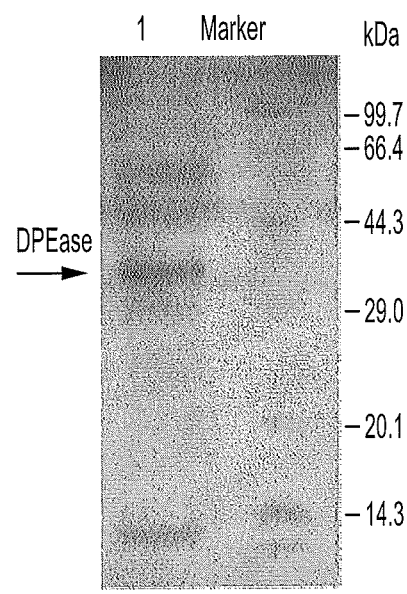
FIG. 3. SDS-PAGE analysis of purified G211S DTEase variant and protein markers stained with Coomassie Blue. Lane 1, *Bacillus subtilis* producing DPEase; Lane 2, protein marker.

The DPEase variants have been expressed in *Bacillus subtilis*, expressed and purified (FIG. 3).

Enzyme properties and kinetic parameters of the wild-type and variants of DPEase from *C. cellulolyticum* for substrate D-psicose have been determined and the results are given in Table 1.

Figure 2:
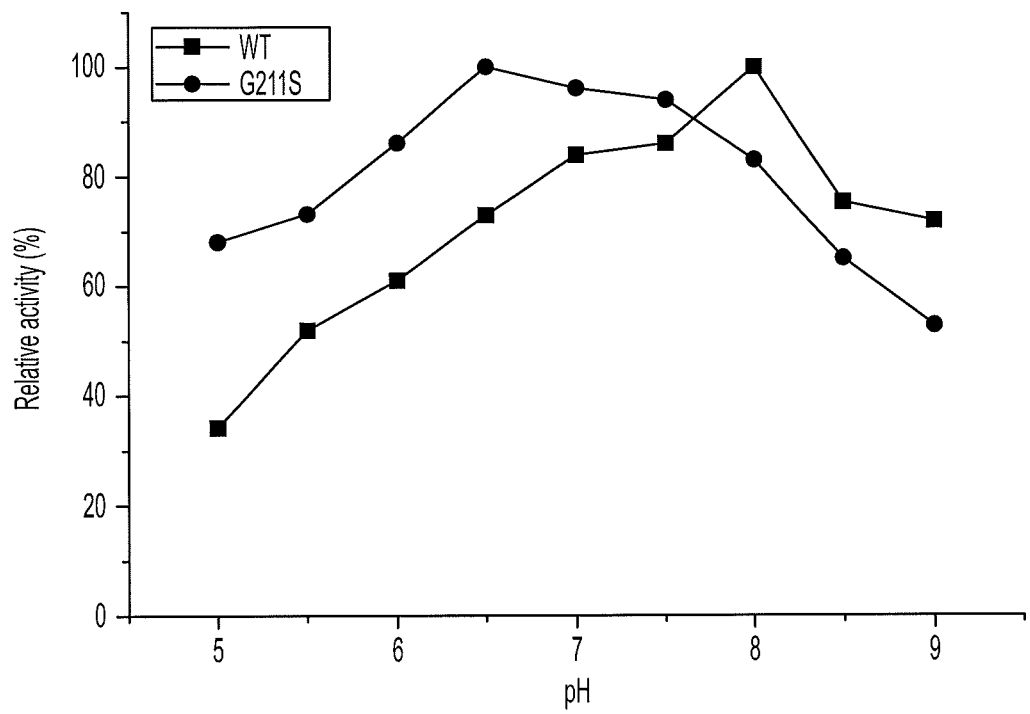
FIG. 2. Comparison of pH profiles between wild-type and G211S mutant of *C. cellulolyticum* DPEase.

The G211S variant showed improved characteristics in comparison with the wild-type DPEase (Table 1), and also with the other known enzymes (Table 2). In particular, it is a weak-acid stable enzyme with more than 80% activity in the pH range from 6 to 8 (FIG. 2), and has a catalysis efficiency of approximately 150.6, and a half-life of at least 10 hours at 55° C. and/or a half-life of at least 6.5 hours at 60° C. In addition, the host is a food-grade microorganism. These attributes are important in the bioproduction of a food-grade D-psicose with a more efficient production cycle and lower production costs.

Materials and Methods

Chemicals and Reagents

Taq DNA polymerase, deoxynucleoside triphosphate (dNTP), chemicals for PCR, T4 DNA ligase and plasmid miniprep kit were obtained from Takara (Dalian, China). The resin for protein purification, the Chelating Sepharose Fast Flow, was obtained from GE (Uppsala, Sweden). Electrophoresis reagents were purchased from Bio-Rad. Isopropyl β-D-1-thiogalactopyranoside (IPTG) and all chemicals used for enzyme assays and characterization were at least of analytical grade, obtained from Sigma (St. Louis, Mo., USA) and Sinopharm Chemical Reagent (Shanghai, China). Oligonucleotides were synthesized by Sangon Biological Engineering Technology and Services (Shanghai, China).

Plasmids, Bacterial Strains, and Culture Conditions

The plasmid pET-22b(+) was obtained from Novagen (Darmstadt, Germany), The *E. coli* DH5α and *E. coli* BL21(DE3) were obtained from Tiangen Biotechnology (Beijing, China). *Bacillus subtilis* WB600 and the plasmid pMA5 were obtained from Invitrogen (Carlsbad, Calif., USA). The bacterial strains were grown in Luria-Bertani medium in a rotary shaker (200 rpm) at 37° C.

Preparation of DPEase Variants of *C. cellulolyticum* in *E. coli*

(1) Primer design for protein modification was as following:

Forward Mutagenic Primers:

```
G211S Forward primer1:
                                          (SEQ ID NO: 12)
CATTTACACACTAGCGAATGTAATCGT
```

-continued

G211A Forward primer2:
(SEQ ID NO: 13)
CATTTACACACTGCCGAATGTAATCGT

G211D Forward primer3:
(SEQ ID NO: 14)
CATTTACACACTGACGAATGTAATCGT

G211R Forward primer4:
(SEQ ID NO: 15)
CATTTACACACTCGCGAATGTAATCGT

G211W Forward primer5:
(SEQ ID NO: 16)
CATTTACACACTTGGGAATGTAATCGT

G211L Forward primer6:
(SEQ ID NO: 17)
CATTTACACACTCTCGAATGTAATCGT

Reverse primer:
(SEQ ID NO: 18)
5'-AGTGTGTAAATGTCCCAAGTAAGAGCCCGC-3'

(2) Amplify the plasmid using the above primers by PCR technique.

Template: pET-Cc-dpe
DNA polymerase: Pfu

PCR program: PCR amplification was performed by Pfu DNA polymerase for 20 cycles consisting of 94° C. for 30 s, 60° C. for 30 s, and 72° C. for 5 min, followed by an extension step of 10 min at 72° C.

(3) After PCR, add 1 μl DpnI restriction enzyme (10 U/μl) into 200 μl PCR product, and incubate at 37° C. for 4 h, to digest and eliminate the template DNA.

(4) The DNA was purified by Gel Extraction Kit.

(5) The 5'-phosphorylation and ligation reactions of mutation fragments were performed together at 16° C. for 12 h, and the reaction system was as follows:

| Mutation DNA | 7.5 μl |
| 10 × T4 ligase buffer | 1 μl |
| PNK | 0.5 μl |
| T4 ligase | 1 μl |

(6) The DNA was transformed into E. coli DH5α. The transformants were selected at 37° C. on the LB agar plates containing 100 μg/mL ampicillin.

(7) The plasmid was extracted and identified by nucleotide sequencing.

(8) The reconstructed plasmid was transformed into E. coli BL21.

The transformants were selected at 37° C. on the LB agar plates containing 100 μg/mL ampicillin.

Preparation of DPEase Variants of C. cellulolyticum in B. subtilis (1) PCR

To subclone the different variant genes to B. subtilis expression plasmid, forward (5'-CGCCATATGAAACATGGTATATACTACGC-3'-SEQ ID NO: 19) and reverse primer (5'-CGCGGATCCTTGTTAGCCGGATCTC-3'-SEQ ID NO: 20) were designed to introduce the NdeI and BamHI restriction sites. Using the reconstructed pET-22b(+) plasmids harboring different DPEase variant genes, PCR amplification was separately performed by Taq Plus DNA polymerase for 35 cycles consisting of 94° C. for 1 min, 60° C. for 1 min, and 72° C. for 1 min, followed by a final extension step of 10 min at 72° C.

(2) Purify the PCR products separately using the Gel Extraction Kit.

(3) The purified PCR products and B. subtilis expression plasmid pMA5 were digested by restriction enzyme NdeI and BamHI (4) DNA fragment and pMA5 were ligated by T4 DNA Ligase, and then the mixture was transformed into E. coli DH5α.

(5) The transformants were selected at 37° C. on the LB agar plates containing 100 μg/mL ampicillin.

(6) The reconstructed plasmids were extracted and identified by restriction enzyme digestion and nucleotide sequencing.

(7) The reconstructed pMA5 plasmids harboring the wild-type or variant DPEase gene were separately transformed into B. subtilis WB600 by electroporation. The transformants were selected at 37° C. on the LB agar plates containing 100 (μg/mL Kanamycin. Purification of DPEase Variants of C. cellulolyticum To purify the recombinant DPEase variants, the centrifuged cell pellets were resuspended in lysis buffer (50 mM Tris-HCl, 100 mM NaCl, pH 7.5) and disrupted by sonication at 4° C. for 6 min (pulsations of 3 s, amplify 90) using a Vibra-Cell 72405 sonicator, and cell debris was removed by centrifugation (20,000 g, 20 min, 4° C.). The cell-free extract was applied onto a Chelating Sepharose Fast Flow resin column (1.0 cm×10.0 cm), previously chelating $Ni^{2+}$, and equilibrated with a binding buffer (50 mM Tris-HCl, 500 mM NaCl, pH 7.5). Unbound proteins were eluted from the column with a washing buffer (50 mM Tris-HCl, 500 mM NaCl, 50 mM imidazole, pH 7.5). Then the DPEase variants were eluted from the column with an elution buffer (50 mM Tris-HCl, 500 mM NaCl, 500 mM imidazole, pH 7.5). The active fractions were pooled and dialyzed overnight against 50 mM Tris-HCl buffer (pH 7.5) containing 10 mM ethylenediaminetetraacetic acid (EDTA) for 48 h at 4° C. Subsequently, the enzyme was dialyzed against 50 mM EDTA-free Tris-HCl buffer (pH 7.5), DPEase Assay The activity was measured by the determination of the amount of produced D-psicose from D-fructose. The reaction mixture of 1 mL contained D-fructose (50 g/L), Tris-HCl buffer (50 mM, pH 8.0), 0.1 mM $Co^{2+}$, and 0.5 μM enzyme. The reaction mixture was incubated at 55° C. for 2 min, and the reaction was stopped after 10 min by boiling. The generated D-psicose was determined by the HPLC method. One unit of enzyme activity was defined as the amount of enzyme catalyzing the formation of 1 μmol of D-psicose/min at 8.0 and 55° C.

Effect of Temperature and pH

The optimum temperature of enzyme activity was measured by assaying the enzyme samples over the range of 35-70° C. for 2 min. Two buffer systems, sodium phosphate (50 mM, pH 6.0-7.0) and Tris-HCl (50 mM, pH 7.5-9.0), were used for measuring the optimum pH of enzyme activity. The thermal stability of the enzyme was studied by incubating the enzyme in Tris-HCl buffer (50 mM, pH 8.0) at various temperatures. At given time intervals, samples were withdrawn and the residual activity was measured under standard assay conditions, To determine the pH stability, the enzyme was incubated at pH 6.0-9.0 at 4° C. for up to 2 h, and the remaining enzyme activity was measured at time intervals under standard assay conditions.

Determination of Kinetic Parameters

Kinetic parameters of DPEase variants were determined in 50 mM Tris-HCl buffer (pH 8.0) containing 0.1 mM $Co^{2+}$ and 5-200 mM substrate for reaction at 55° C., The enzyme reactions were stopped after 10 min by boiling, and the amount of D-psicose was determined by the HPLC assay.

Kinetic parameters, such as the Michaelis-Menten constant ($K_m$) and turnover number ($k_{cat}$) values for substrates, were obtained using the Lineweaver-Burk equation and quantification of enzyme concentration.

Analytical Methods

The concentrations of D-fructose and D-psicose were analyzed by HPLC equipped with a refractive index detector and a $Ca^{2+}$ tcarbohydrate column (Waters Sugar-Pak 1, Waters Corp., Milford, Mass.), which was eluted with water at 85° C. and 0.4 mL/min. Protein concentration was determined according to the method of Bradford using bovine serum albumin as a standard. SDS-PAGE was carried out according to the method of Laemmli. Gels (12% w/v polyacrylamide) were stained with Coomassie Brilliant Blue and destained with an aqueous mixture of 10% (v/v) methanol/ 10% (v/v) acetic acid.

TABLE 1

Enzyme properties and kinetic parameters of the wild-type and mutant enzymes of DPEase from *C. cellulolyticum* for substrate D-psicose

| Enzyme | Optimum pH | Optimum temp, (° C.) | Equilibrium ratio between D-psicose and D-fructose at 55° C. | Half-life at 60° C. (h) | $K_{cat}/K_m$ for D-fructose ($mM^{-1}\ min^{-1}$) |
|---|---|---|---|---|---|
| Wild type | 8.0 | 55 | 32:68 | 6.8 | 62.7 |
| G211S | 6.5 | 55 | 33:67 | 7.2 | 150.6 |
| G211A | 8.5 | 50 | 30:70 | 2.5 | 9.8 |
| G211D | 8.0 | 60 | 32:68 | 5.3 | 86.7 |
| G211R | 6.5 | 45 | 28:72 | 3.7 | 26.5 |
| G211W | 7.0 | 60 | 32:68 | 5.9 | 68.1 |
| G211L | 8.0 | 55 | 30:70 | 6.7 | 73.2 |

[a]NR, not reported.

TABLE 2

Enzyme properties and kinetic parameters of DTEase family enzymes for D-psicose production

| DTEase family enzymes | Optimum pH | Optimum temp, (° C.) | Equilibrium ratio between D-psicose and D-fructose | Half-life (thermo-stability) | $K_{cat}/K_m$ for D-fructose ($mM^{-1}\ min^{-1}$) | Reference |
|---|---|---|---|---|---|---|
| *C. cellulolyticum* DPEase mutant of G211S | 6.5 | 55 | 33:67 (55° C.) | 10.1 h (55° C.) 7.2 h (60° C.) | 150.6 | Invention |
| *C. cellulolyticum* DPEase | 8.0 | 55 | 32:68 (55° C.) | 9.5 h (55° C.) 6.8 h (60° C.) | 62.7 | Mu et al. 2011 |
| *Clostridium* sp. DPEase | 8.0 | 65 | 28:72 (65° C.) | 0.25 h[b] (60° C.) | 58.7 | Mu et al. 2013 |
| *C. bolteae* | 7.0 | 55 | 32:68 (60° C.) | 2.6 h[b] (55° C.) | 59.4[c] | Jia et al. 2013 |
| *C. scindens* | 7.5 | 60 | 28:72 (50° C.) | 1.8 h[b] (50° C.) | 8.72 | Zhang et al. 2013 |
| *Ruminococcus* sp. DPEase | 7.5-8.0 | 60 | 28:72 | 1.6 h (60° C.) | 16 | Zhu et al. 2012 |
| *A. tumefaciens* DPEase | 8.0 | 50 | 32:68 (30° C.) 33:67 (40° C.) | 8.90 min (55° C.) 3.99 min (60° C.) | 85 | Kim et al. 2006 |
| *A. tumefaciens* DPEase mutant of S213C | NR[a] | NR | NR | 0.46 h (55° C.) | 101 | Choi et al. 2011 |
| *A. tumefaciens* DPEase mutant of I33L | NR | NR | NR | 1.06 h (55° C.) | 105 | Choi et al, 2011 |
| *A. tumefaciens* DPEase mutant of S213C + I33L | NR | NR | NR | 4.4 h (55° C.) | 134 | Choi et al, 2011 |
| *Rhizobium* DTEase | 9.0-9.5 | 50 | 23:77 | NR | NR | Maruta et al. 2010 |
| *P. cichorii* DTEase | 7.5 | 60 | 20:80 (30° C.) | 1 h (50° C.) | NR | Itoh et al, 1994 |
| *R. sphaeroides* DTEase | 9.0 | 40 | 23:77 (40° C.) | NR | NR | Zhang et al. 2009 |

[a]NR, not reported,
[b]The half-life values were converted from the original references with the unit of min.
[c]The value was converted from the original reference with the unit of $mM^{-1}\ s^{-1}$.

EXAMPLE 2

Chromosomal Integration and Production of Microbial Strain Producing D-psicose Epimerase The inventors constructed five strains with chromosomal integration of D-psicose epimerase. To avoid antibiotic addition and antibiotic-resistant gene (ARG) within the strain, the strains were constructed by chromosomal integration without inserting ARG by two approaches, i.e., Cre/Lox and mazF-based systems. The Cre/Lox system is to construct a strain with chromosomal integration with ARG and knock it out by Cre recombinase (Approach 1). The other is to construct a strain with chromosomal integration with the mazF gene and knock it out by the p43-DPE gene (Approach 2). Three strains of *Bacillus subtilis* were used as host strains, i.e., 1A751, WB600, and WB800.

Approach 1. Cre/Lox System-Based Genome Engineering in *Bacillus subtilis*

1.1 Introduction

The Cre/Lox recombination system is a simple two-component system currently recognized as a powerful DNA recombination tool. The general principle behind the Cre/Lox system relies upon the ability of Cre recombinase to identify, bind and recombine DNA between two loxP sites; each of these 34 bp target DNA sequences consists of two 13 bp inverted repeat sequences, flanking a central, 8 bp, directional core. By using the Cre/Lox recombination system, the antibiotic-resistant gene (ARG) was knocked out.

1.2 Methods

Based on Cre/Lox recombination system, to construct a strain with chromosomal integration without ARG contains several steps as follows (see also FIG. 4):

a. Splice DPEase-Coding Gene with Promoter p43 by Overlap Extension PCR.

Promoter p43 and DPEase-coding gene were spliced by overlap extension PCR. Then the PCR-produced p43-DPE cassette was cloned into pMD19-T to create pP43DPE.

b. Insert p43-DPE Gene (p43-DPE') and Pectinomycin-Resistant Gene (lox71-spc-lox66) Into Shuttle Plasmid Vector pDGIEF to Build a Reconstructed Plasmid pDGI-7S6-DPE.

Figure 4:
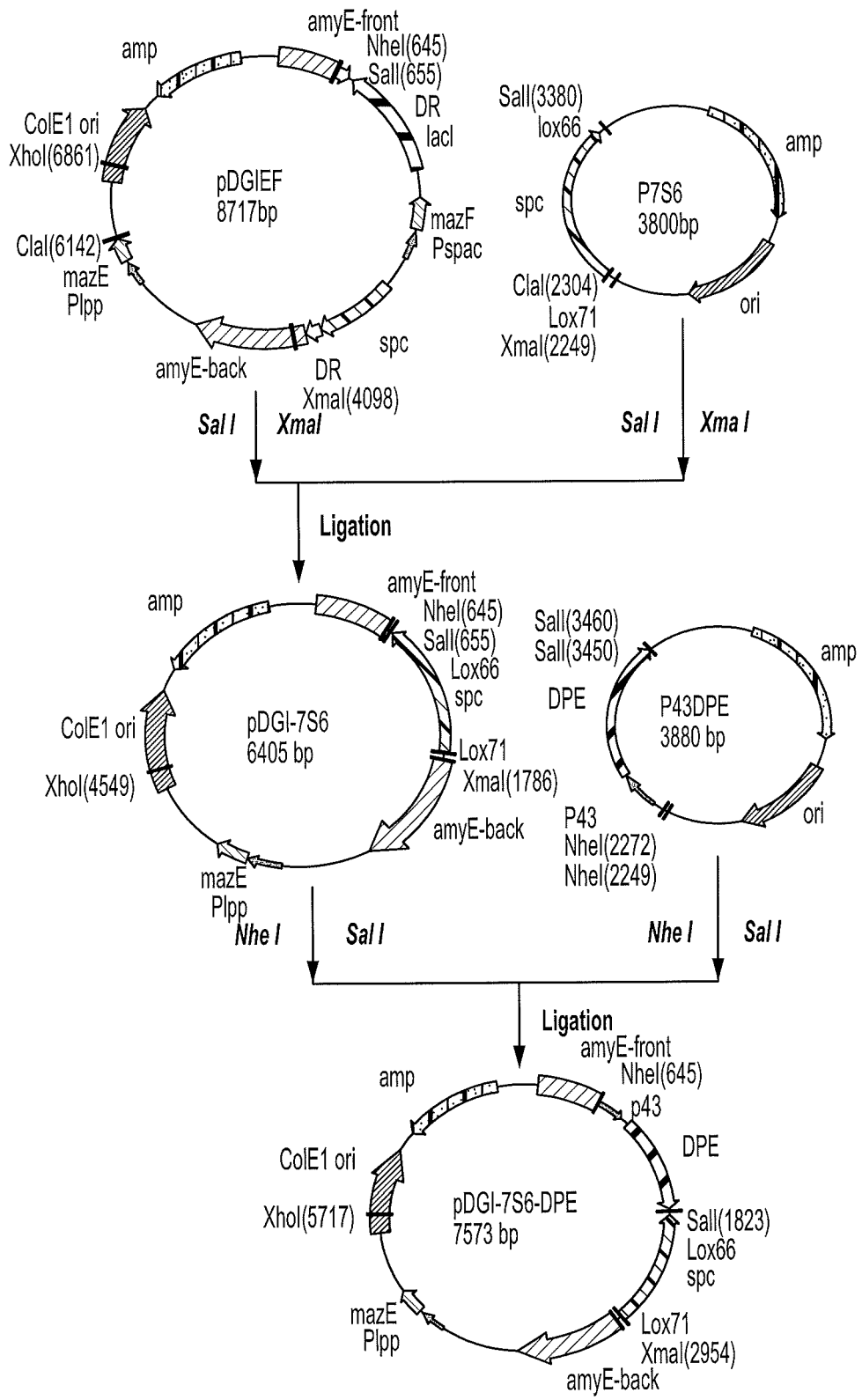
FIG. 4 shows the construction of plasmid pDGI-756-DPE used for inserting DPEase gene in *Bacillus subtilis* strains according to approach 1 (Cre/Lox recombination system) described in Example 2.
Figure 5:
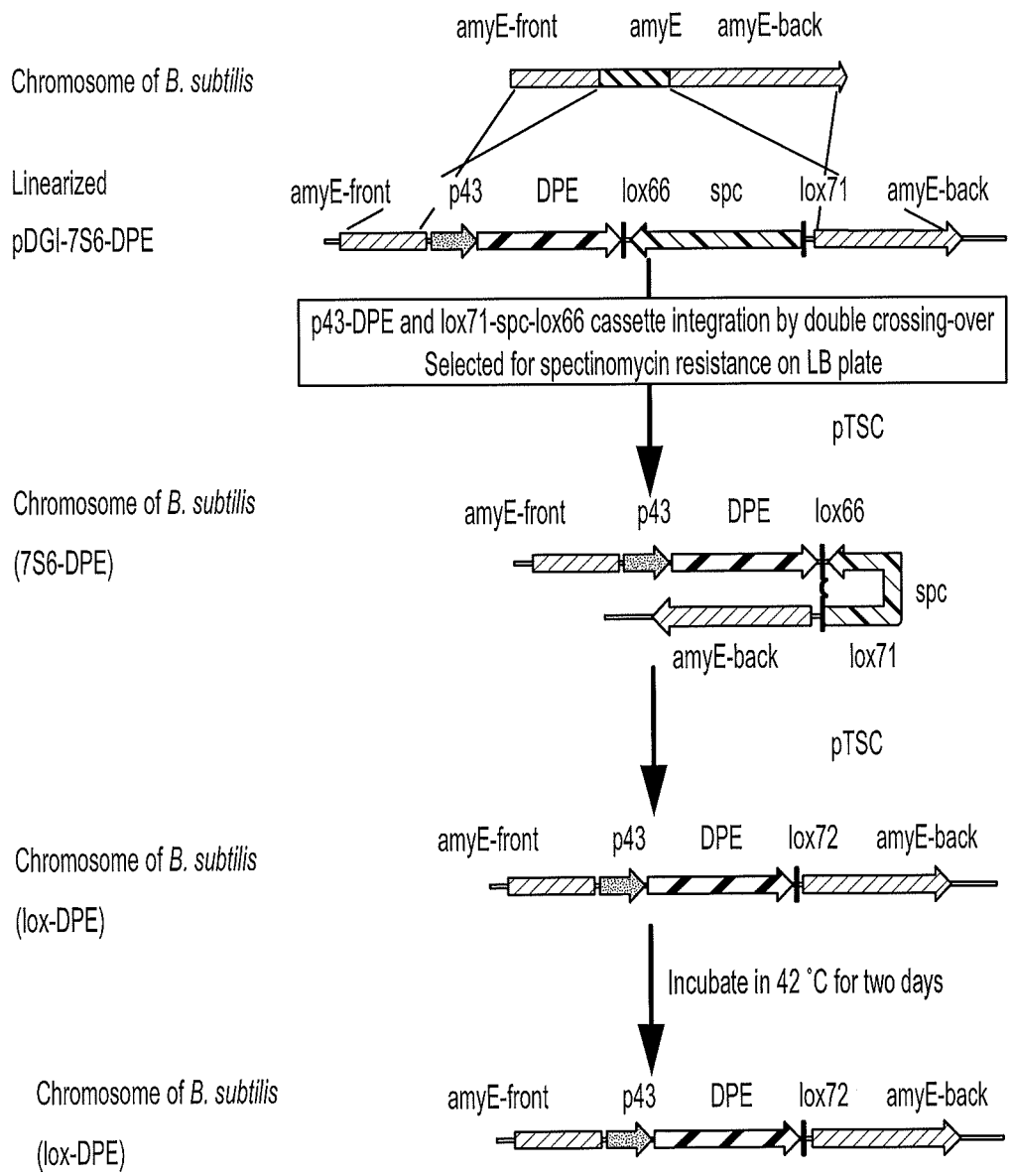
FIG. 5 shows the main steps of approach 1 described in Example 2 to produce DPEase-expressing *B. subtilis* strains.

Plasmid pDGI-7S6-DPE was constructed as follows. The SaiI- and XmaI-flanked fragment containing the lox71-spc-lox66 cassette was transferred from p7S6 to the corresponding sites of pDGIEF, giving pDGI-7S6; then NheI/Sa/I digested pP43DPE was cloned into the corresponding sites of pDGI-7S6 to yield pDGI-7S6-DPE (Figure. 4).

c. Transform the Reconstructed Plasmid into *B subtilis* for Chromosomal Integration.

The pDGI-7S6-DPE plasmid was linearized by XhoI and transformed into *B. subtilis* strains (1A751, WB600, and WB800) by chemical transformation (Keith et al., *Appl Microbiol Biotechnol*, 2013, 97:6803-6811 (host 1A751); Zhang et al., *Bioresource Technology*, 2013, 146: 543-548 (host WB600); Nguyen et al., *Microbial Cell Factories*, 2013, 12:79 (host WB800)). *B. subtilis* amylase gene homologous arms were used to homologously recombine between the integration vector and chromosomal DNA. Through chromosomal integration, the p43-DPE cassette and lox71-spc-lox66 cassette were inserted into the chromosomal DNA.

d. Screen the Integrated *B. subtilis* by Spectinomycin.

The recombinant strains were screened on the LB plate with 100 μg/mL Spectinomycin.

e. Transform the pTSC Plasmid into *B. subtilis* (7S6-DPE), and Then Were Screened by Erythromycin.

pTSC plasmid harbored Cre recombinase gene was transformed into *B. subtilis* (pDGI-7S6-DPE) competent cells. The *B. subtilis* (7S6-DPE, pTSC) strains were screened on the LB plate with 200 ug/mL Erythromycin.

f. Screen *B. subtilis* (lox-DPE, pTSC) strains by Erythromycin and Spectinomycin.

If the Spectinomycin-resistant gene was knocked out, the strains could not grow on the LB plate with 200 ug/mL Erythromycin and 100 μg/mL Spectinomycin, but could grow on the LB plate with 200 ug/mL Erythromycin. Based on this, *B. subtilis* (lox-DPE, pTSC) strains were screened and selected.

g. Screen *B. subtilis* (lox-DPE) strains by Erythromycin.

pTSC was a temperature-sensitive plasmid which cannot replicate when the plate was incubated in 42° C. If the pTSC plasmid was lost in *B. subtilis* strains, the strains could not grow on the LB plate with 200 ug/mL Erythromycin, After incubation in 42° C. for two days, *B. subtilis* (lox-DPE) strains were screened and selected on the LB plate and LB plate with 200 ug/mL Erythromycin.

h. Validate for Knock-Out of Antibiotic Resistant Gene.

Two test methods were used to validate for knock-out of antibiotic resistant gene, PCR and screening on antibiotic plates. The PCR amplification was performed using the primers of the *B. subtilis* amylase homologous arms gene. The DNA fragment was sequenced and aligned with the antibiotic resistant gene sequence to make sure the antibiotic resistant gene was knocked out. Meanwhile, the primers of the antibiotic resistant gene were also used. If the PCR amplification was failed, the antibiotic resistant gene did not exist in the constructed strains. The other test method was screening on antibiotic plates. If the strains could not grow on antibiotic plates, the antibiotic resistant gene was knocked out.

Approach 2. mazF-Based Genome Engineering in *Bacillus subtilis*

2.1 Introduction mazF is an *Escherichia coli* toxin gene which can be used as a novel counter-selectable marker for unmarked chromosomal manipulation in *Bacillus subtilis*. mazF was placed under the control of a xylose-inducible expression system. The *Bacillus subtilis* strains harboring the mazF cassette cannot grow on the xylose-containing medium. If the mazF cassette is replaced by the p43-DPE cassette, the strains can grow on the xylose-containing medium.

2.2 Methods

Figure 7:
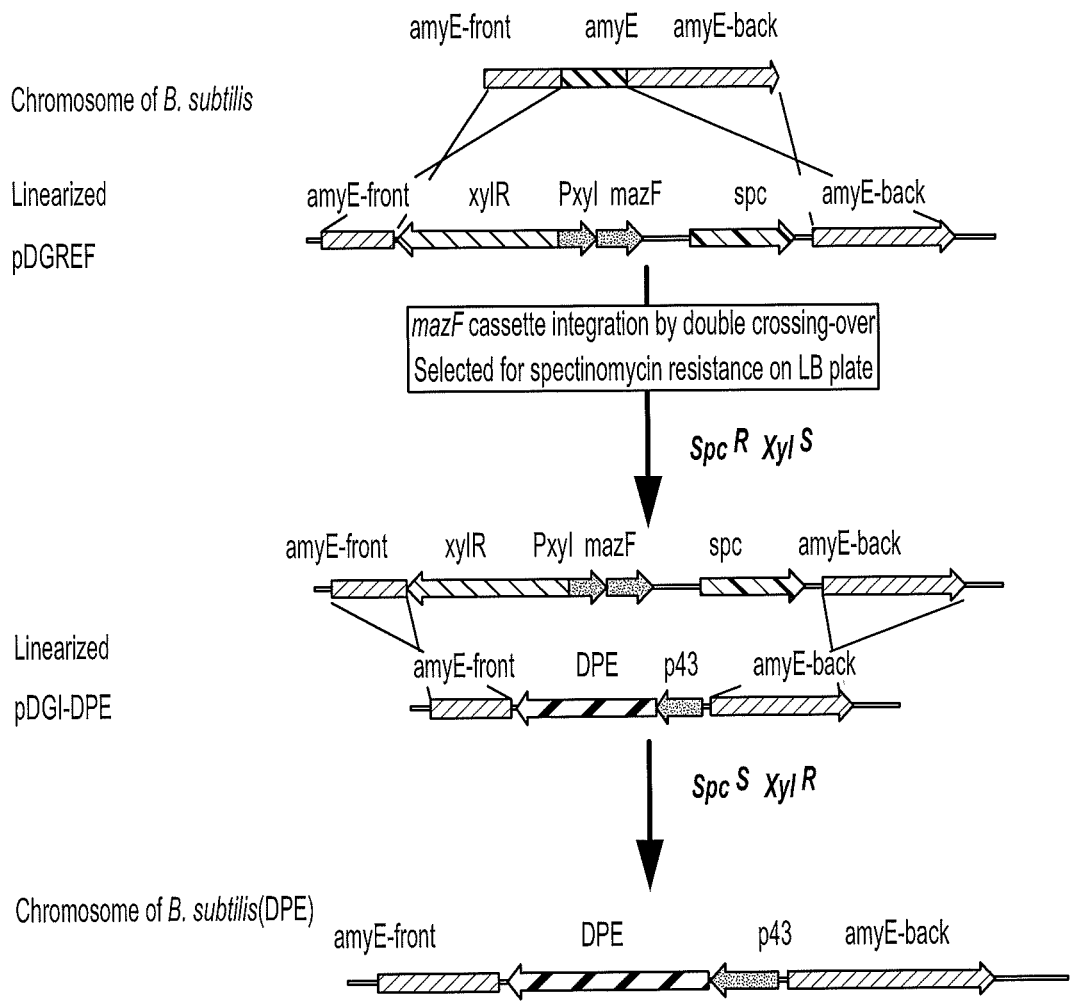
FIG. 7 shows the main steps of approach 2 described in Example 2 to produce DPEase-expressing *B. subtilis* strains.

Based on this, unmarked chromosomal integration in *Bacillus subtilis* contains several steps as follows (see also FIG. 7):

a. Insert p43-DPE Gene (p43-DPE) into Shuttle Plasmid Vector pDGIEF to Build a Reconstructed Plasmid pDGI-DPE.

Figure 6:
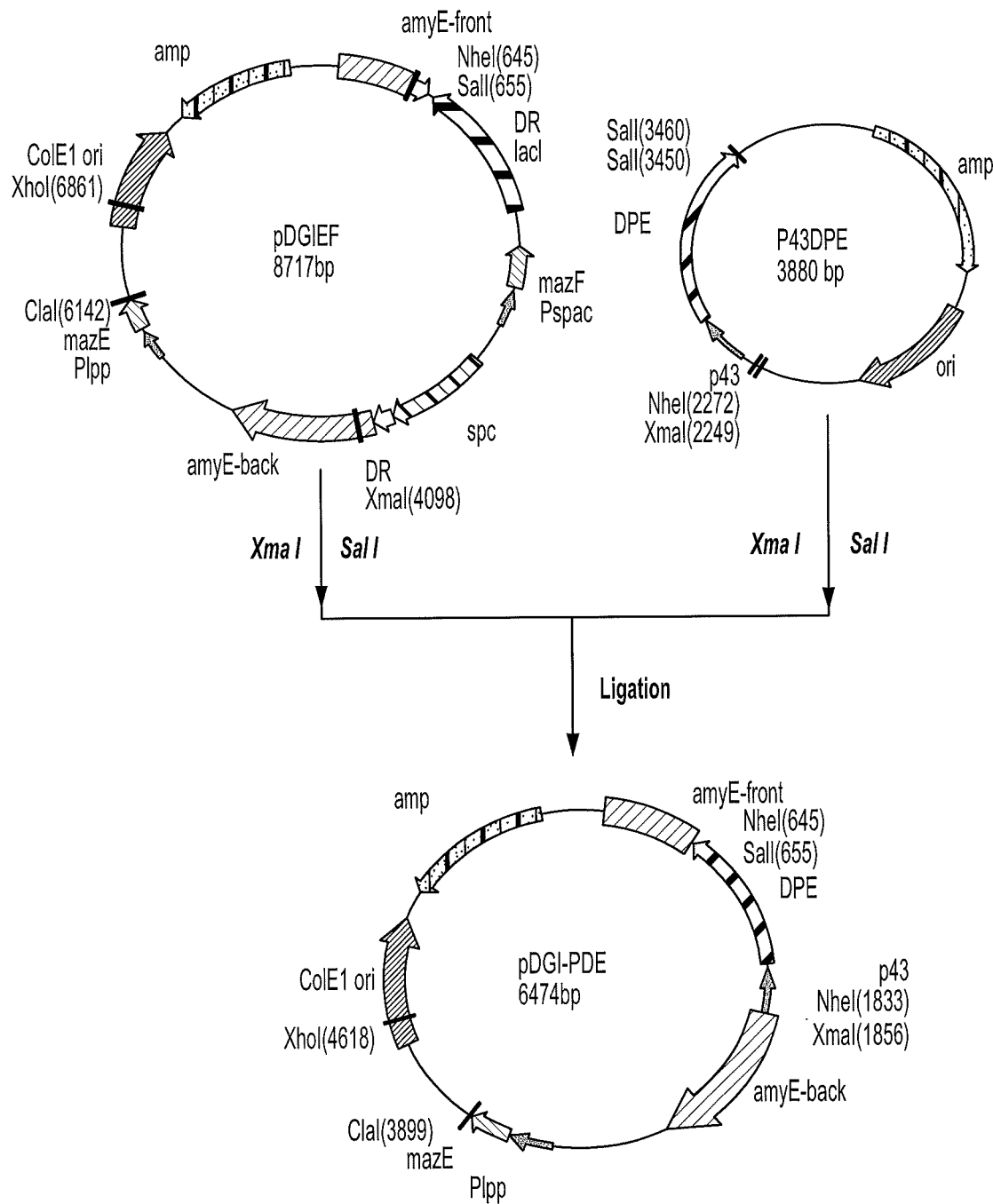
FIG. 6 shows the construction of plasmid pDGI-DP used for inserting the DPEase gene in *Bacillus subtilis* strains according to approach 2 (mazF-based system) described in Example 2.

Plasmid pDGI-DPE was constructed as follows. The Xma I- and Sal I-flanked fragment containing the p43-DPE cassette was transferred from pP43DPE to the corresponding sites of pDGIEF, giving pDGI-DPE (FIG. 6).

b. Transform the Reconstructed Plasmid pDGREF into *B. subtilis* for Chromosomal Integration.

The pDGREF plasmid was linearized by Cla I and transformed into *B. subtilis* strains (1A751, WB600, WB800) by chemical transformation, *B. subtilis* amylase gene homologous arms were used to homologously recombine between the integration vector and chromosomal DNA. Through chromosomal integration, the mazF cassette was inserted into the chromosomal DNA.

c. Screen the Integrated *B. subtilis* by Spectinomycin and Xylose.

The recombinant strains were screened on the LB plate with 100 μg/mL Spectinomycin. Then the positive clones were streaked on the Spectinomycin (100 μg/mL)-xylose (2%)-containing LB plate and Spectinomycin (100 ug/mL)-containing LB plate, respectively. The positive clones which could not grow on the xylose-containing plate were used for the next step.

d. Transform the pDGI-DPE Plasmid into *B. subtilis* (REF), and Then Were Screened by Xylose.

pDGI-DPE plasmid harbored p43-DPE gene was linearized by Xho I and transformed into *B. subtilis* (REF) competent cells. The *B. subtilis* (DPE) strains were screened on the LB plate with 2% xylose.

Results

Five strains were selected by these two approaches. After the *B. subtilis* strains were selected, the strains were fermented in lab medium. The enzyme activity was determined as described in Example 1, to ensure the DPEase-coding gene was inserted into the chromosomal DNA. Enzyme activity was determined for all the selected strains. The highest enzymatic activity was detected for the 1A751 strain. The enzymatic activity reached 03.45 U/mL, which was close to the initial activity detected for the plasmid-dependent *B. subtilis*.

| | Plasmid replicative | Approach 1 | | Approach 2 | |
|---|---|---|---|---|---|
| Host | WB600 | 1A751 | WB600 | WB800 | 1A751 | WB600 |
| Enzyme activity (U/mL) | ~5 | 3.43 | 1.39 | 0.40 | 3.45 | 1.40 |

SEQUENCE LISTING TABLE

| SEQ ID NO: | Description |
|---|---|
| 1 | Nucleic acid sequence of the parent D-psicose 3-epimerase from *Clostridium cellulolyticum* |
| 2 | Amino acid sequence of the parent D-psicose 3-epimerase from *Clostridium cellulolyticum* |
| 3 | Nucleic acid sequence of the D-psicose 3-epimerase variant derived from *Clostridium cellulolyticum* |
| 4 | Amino acid sequence of the D-psicose 3-epimerase variant derived from *Clostridium cellulolyticum* |
| 5 | Amino acid sequence of *Clostridium* sp. DPEase |
| 6 | Amino acid sequence of *C. scindens* DPEase |
| 7 | Amino acid sequence of *A. tumefaciens* DPEase |
| 8 | Amino acid sequence of *Ruminococcus* sp. DPEase |
| 9 | Amino acid sequence of *C. bolteae* DPEase |
| 10 | Amino acid sequence of *P. cichorii* DTEase |
| 11 | Amino acid sequence of *R. sphaeroides* DTEase |
| 12-20 | Primers |

The invention claimed is:

1. A variant of a parent D-psicose 3-epimerase, wherein the variant comprises a substitution of a Glycine residue by a Serine residue at a position corresponding to position 211 in SEQ ID NO: 2 compared to the parent D-psicose 3-epimerase, said variant comprising, D-psicose 3-epimerase activity to modify D-fructose into D-psicose with greater catalysis efficiency than parent D-psicose 3-epimerase, the parent D-psicose 3-epimerase having an amino acid sequence with at least 85% identity with a sequence selected from the group consisting of SEQ ID NO: 2 and 5-10, and said variant has an amino acid sequence having at least 80% identity with a sequence selected from the group consisting of SEQ ID NO: 2 and 5-10.

2. The variant according to claim 1, wherein the variant has one or several of the following features:
   a) a lower pH optimum compared to the parent D-psicose 3-epimerase;
   b) a higher catalysis efficiency to the substrate D-fructose compared to the parent D-psicose 3-epimerase; and
   c) a longer half-life at 60° C. compared to the parent D-psicose 3-epimerase,
   wherein the parent D-psicose 3-epimerase is a D-psicose 3-epimerase that is identical to the variant except that a Glycine residue is present at a position corresponding to position 211 in SEQ ID NO: 2.

3. The variant according to claim 1, wherein the variant has an amino acid sequence having at least 85% identity with a sequence selected from the group consisting of SEQ ID NO: 2 and 5-10.

4. The variant according to claim 1, wherein the parent D-psicose 3-epimerase is selected from a D-tagatose 3-epimerase from *Pseudomonas cichorii*, a D-psicose 3-epimerase from *Agrobacterium tumefaciens*, a D-psicose 3-epimerase from *Clostridium* sp., a D-psicose 3-epimerase from *Clostridium scindens*, a D-psicose 3-epimerase from *Clostridium bolteae*, a D-psicose 3-epimerase from Ruminococcus sp., and a D-psicose 3-epimerase from *Clostridium cellulolyticum*.

5. The variant according to claim 4, wherein the parent D-psicose 3-epimerase is the D-psicose 3-epimerase from *Clostridium cellulolyticum*.

6. The variant according to claim 5, wherein the variant comprises SEQ ID NO: 4 or an amino acid sequence having at least 90% identity with SEQ ID NO: 4 with a Ser at position 211.

7. The variant according to claim 4, wherein the variant comprises SEQ ID NO: 5 with a G211S substitution or an amino acid sequence having at least 85% identity with SEQ ID NO: 5 and having a Serine at position 211.

8. The variant according to claim 4, wherein the variant comprises SEQ ID NO: 6 with a G210S substitution or an amino acid sequence having at least 85% identity with SEQ ID NO: 6 and having a Serine at position 210.

9. The variant according to claim 4, wherein the variant comprises SEQ ID NO: 7 with a G211S substitution or an amino acid sequence having at least 85% identity with SEQ ID NO: 7 and having a Serine at position 211.

10. The variant according to claim 4, wherein the variant comprises SEQ ID NO: 8 with a G213S substitution or an amino acid sequence having at least 85% identity with SEQ ID NO: 8 and having a Serine at position 213.

11. The variant according to claim 4, wherein the variant comprises SEQ ID NO: 9 with a G223 S substitution or an amino acid sequence having at least 85% identity with SEQ ID NO: 9 and having a Serine at position 223.

12. The variant according to claim 4, wherein the variant comprises SEQ ID NO: 10 with a G213S substitution or an amino acid sequence having at least 85% identity with SEQ ID NO: 10 and having a Serine at position 213.

13. The variant according to claim 1, wherein the variant and the parent D-psicose 3-epimerase respectively have an amino acid sequence with at least 95% identity with a sequence selected from the group consisting of SEQ ID NO: 2 and 5-10.

14. The variant according to claim 1, wherein the variant and the parent D-psicose 3-epimerase respectively have an amino acid sequence with at least 90% identity with a sequence selected from the group consisting of SEQ ID NO: 2 and 5-10.

15. An enzymatic composition comprising a D-psicose 3-epimerase variant according to claim 1 and an additional enzyme.

16. An isolated nucleic acid encoding a variant according to claim 1.

17. A recombinant expression vector comprising a nucleic acid according to claim 16.

18. A recombinant host cell comprising a nucleic acid according to claim 16 or a recombinant expression vector comprising said nucleic acid.

19. The recombinant host cell according to claim 18, wherein the nucleic acid encoding said variant is integrated into the host cell's chromosome.

20. The recombinant host cell according to claim 18, wherein the host cell is a GRAS strain (Generally Recognized As Safe).

21. The recombinant host cell according of claim 20, wherein the host cell is a *Bacillus subtilis* strain in which the gene encoding for bacillopeptidase F is inactivated.

22. A food product comprising a host cell according to claim 20.

23. A method for producing a D-psicose 3-epimerase variant comprising culturing the recombinant host cell according to claim 18, and optionally recovering the produced D-psicose 3-epimerase variant from the resulting culture.

24. A method for producing D-psicose comprising contacting a variant according to claim 1 with D-fructose in conditions suitable for the D-psicose 3-epimerase activity and optionally recovering produced D-psicose.

25. The method according to claim 24, wherein the D-fructose is previously or simultaneously produced by a glucose isomerase from D-glucose.

* * * * *